US010962477B2

(12) United States Patent
Won et al.

(10) Patent No.: US 10,962,477 B2
(45) Date of Patent: Mar. 30, 2021

(54) WIDE-ANGLE EMISSION FILTER, OPTICAL SENSOR ASSEMBLY HAVING THE SAME, PCR SYSTEM HAVING THE SAME, AND METHOD OF MANUFACTURING THE SAME

(71) Applicant: OPTOLANE Technologies Inc., Seongnam-shi (KR)

(72) Inventors: Jun Ho Won, Namyangju-shi (KR); Do Young Lee, Seoul (KR); Kyung Hak Choi, Yongin-shi (KR); An Shik Choi, Seoul (KR)

(73) Assignee: OPTOLANE TECHNOLOGIES INC., Seongnam (KR)

( * ) Notice: Subject to any disclaimer, the term of this patent is extended or adjusted under 35 U.S.C. 154(b) by 320 days.

(21) Appl. No.: 15/831,837

(22) Filed: Dec. 5, 2017

(65) Prior Publication Data
US 2018/0156731 A1    Jun. 7, 2018

(30) Foreign Application Priority Data

Dec. 6, 2016 (KR) ........................ 10-2016-0164825

(51) Int. Cl.
*G01N 21/64* (2006.01)
*G01N 21/21* (2006.01)
(Continued)

(52) U.S. Cl.
CPC ...... *G01N 21/6428* (2013.01); *B01L 3/50851* (2013.01); *C12Q 1/686* (2013.01);
(Continued)

(58) Field of Classification Search
CPC ................ G01N 21/01; G01N 21/64; G01N 2021/6463; G02B 5/20; G02B 5/28;
(Continued)

(56) References Cited

U.S. PATENT DOCUMENTS 6,816,636 B2 * 11/2004 Cole .................. G01J 3/26
                                             349/198
6,893,781 B2   5/2005 Nonaka et al.
(Continued)

FOREIGN PATENT DOCUMENTS

CN   1318593   10/2001
CN   1428639   7/2003
(Continued)

OTHER PUBLICATIONS

Exteneded European Search Report for European Application No. EP 17 20 5204, dated May 18, 2018.

*Primary Examiner* — Michael L Hobbs
(74) *Attorney, Agent, or Firm* — Kile Park Reed & Houtteman PLLC

(57) ABSTRACT

The wide-angle emission filter includes a base matrix, a photoresist, and a colorant. The base matrix has a flat shape and including a transparent material. The base matrix does not generate fluorescent light or phosphorescent light by an excitation light. The photoresist is disposed in the base matrix. The photoresist is fixed in a solid state through at least one method selected from the group consisting of thermal hardening, photo hardening, and drying. The colorant is disposed in the base matrix and includes light having a predetermined wavelength range. The wide-angle emission filter filters the excitation light regardless of an incident angle of the excitation light.

11 Claims, 19 Drawing Sheets

(51) Int. Cl.
*B01L 3/00* (2006.01)
*C12Q 1/686* (2018.01)
*G01J 3/51* (2006.01)
*G01J 3/02* (2006.01)
*G01J 1/02* (2006.01)
*G01J 1/04* (2006.01)
*G01J 3/44* (2006.01)
*G01J 3/443* (2006.01)
*G02B 5/22* (2006.01)
*G01J 3/46* (2006.01)

(52) U.S. Cl.
CPC .......... *G01J 1/0252* (2013.01); *G01J 1/0488* (2013.01); *G01J 3/0286* (2013.01); *G01J 3/443* (2013.01); *G01J 3/4406* (2013.01); *C12Q 1/51* (2013.01); *G01N 21/21* (2013.01); *G02B 5/223* (2013.01); *G01J 2003/468* (2013.01); *G01N 2021/6471* (2013.01)

(58) Field of Classification Search
CPC ....... B01L 2300/0627; B01L 2200/147; B01L 2200/10; G03F 7/0002; G03F 7/70225; G03F 7/002; G03F 7/0225
See application file for complete search history.

(56) References Cited

U.S. PATENT DOCUMENTS

| | | |
|---|---|---|
| 9,798,183 B2 | 10/2017 | Kimura et al. |
| 10,279,352 B2 | 5/2019 | Lee et al. |
| 2002/0034696 A1* | 3/2002 | Wolf ................. C09B 45/14 430/7 |
| 2003/0179327 A1 | 9/2003 | Nonaka et al. |
| 2005/0142467 A1 | 6/2005 | Komatsu et al. |
| 2005/0237524 A1* | 10/2005 | Kamei ............... G01N 21/6428 356/318 |
| 2009/0096051 A1 | 4/2009 | Sugiyama et al. |
| 2009/0246651 A1 | 10/2009 | Fujimori et al. |
| 2010/0055666 A1* | 3/2010 | Wimberger-Friedl ................. G01N 21/6454 435/4 |
| 2010/0196206 A1 | 8/2010 | Lee et al. |
| 2016/0271611 A1 | 9/2016 | Lee et al. |

FOREIGN PATENT DOCUMENTS

| | | |
|---|---|---|
| CN | 1637618 | 7/2005 |
| CN | 101114123 | 11/2011 |
| CN | 103221849 | 7/2013 |
| CN | 104903784 | 11/2017 |
| CN | 105985905 | 2/2020 |
| DE | 602 09 665 | 12/2006 |
| EP | 2 626 393 | 8/2013 |
| JP | 2009-99591 | 5/2009 |
| KR | 10-0822672 | 4/2008 |

* cited by examiner

WIDE-ANGLE EMISSION FILTER, OPTICAL SENSOR ASSEMBLY HAVING THE SAME, PCR SYSTEM HAVING THE SAME, AND METHOD OF MANUFACTURING THE SAME

CROSS-REFERENCE TO RELATED APPLICATION(S)

This application claims priority under 35 USC § 119 to Korean Patent Applications No. 10-2016-0164825, filed on Dec. 6, 2016 in the Korean Intellectual Property Office (KIPO), the contents of which are incorporated herein in its entirety by reference.

BACKGROUND

1. Technical Field

Example embodiments relate generally to a wide-angle emission filter, an optical sensor assembly having the same, a PCR system having the same, and a method of manufacturing the same. More particularly, embodiments of the inventive concept relate to a wide-angle emission filter having uniform filtering characteristics regardless of incident angles, an optical sensor assembly having the same, a PCR system having the same, and a method of manufacturing the same.

2. Description of the Related Art

An optical filter is a member configured to transform optical characteristics of an incident light and to emit the transformed light. The optical filters are classified into an interference filter, an absorption filter, a polarizing filter, a spatial filter, etc., based on optical characteristics.

The interference filter is called as a color filter, and transmits only a predetermined wavelength range. For example, the interference filter transmits light having a wavelength smaller than a predetermined wavelength, but blocks light having a wavelength greater than the predetermined wavelength. Basic principle of the interference filter is based on interference phenomenon of light. In the interference filter, a plurality of dielectric films are stacked to determine wavelength of transmitting light.

The absorption filter decreases quantum efficiency of light detected by optical sensors. The absorption filter controls transmittance of light in a relatively wide wavelength range. Interference or scattering of light is small in the absorption filter. Absorption filters are usually made from glass to which various inorganic or organic compounds have been added. These compounds absorb some wavelengths of light while transmitting others. The compounds can also be added to plastic (often polycarbonate or acrylic) to produce gel type filters, which are lighter and cheaper than glass-based filters.

The polarizing filter transforms polarizing characteristics of incident light, and is formed using a polarizing plate. The spatial filter is used to remove noise spatially distributed in light flux.

Among the described filters, since the interference filter transmits only a predetermined wavelength, the interference filter is widely used for an optical sensor. That is, when light having a wavelength, which is different from a wavelength to be detected, is incident into the optical sensor, the light having the wavelength to be detected is mixed with the light having different wavelength, and thus, sensing efficiency of the optical sensor is decreased by the noise caused by the light having different wavelength. The interference filter only transmits the light having the wavelength to be detected, but blocks the light having different wavelengths, and thus, sensitivity of the optical sensor is improved and accuracy of a sensing device is improved.

A conventional interference filter is formed by attaching metal such as a silver thin film on a surface of an optical glass or formed by alternately stacking transparent thin films having different refractive indexes. In particular, the interference filter formed by alternately stacking the transparent thin films having different refractive indexes has excellent optical characteristics, such as substantially square optical characteristics in transmission spectroscopy.

An emission filter transmits emission light such as fluorescent light, phosphorescent light, etc., having long wavelength, and blocks excitation light having short wavelength. The emission filter is used for a sensing device using the fluorescent light, the phosphorescent light, etc. The interference filter has excellent optical characteristics in blocking or transmitting light based on a predetermined wavelength, and thus, widely is used for the emission filter.

However, the emission filter has excellent filtering characteristics in a light incident into an upper surface of the emission filter in a vertical direction, but has poor filtering characteristics for light incident into the upper surface of the emission filter in an inclined direction. The reason of the above phenomenon is that optical characteristics of the interference filter is changed based on a distance between adjacent interfaces of the transparent thin films, and the distance between the adjacent interfaces is changed based on the incident angle of the incident light.

In particular, when the excitation light incident into a specimen is scattered, a portion of the scattered excitation light transmits the emission filter, and thus, noise is increased. When an amount of the emission light is greater than an amount of the excitation light by enough amount, the emission light can be sensed by the optical sensor. However, when the amount of the emission light is smaller than the amount of the excitation light, the emission light may not be detected by the noise. In particular, the above-mentioned problem is increased, when a size of the specimen is small and a distance between the optical sensor and the specimen is decreased.

By the above-mentioned problem, an optical part occupies a large volume, for example 80%, in a sensing device for sensing the emission light such as a polymerase chain reaction (PCR) device, a fluorescent activated cell sorter (FACS), a Western blot device, etc. Thus, the sensing device does not have mobility, and point-of-care is impossible. Also, price of the sensing device is very expensive. Furthermore, error is generated during transporting or relocation of the sensing device, and thus, a lot of time is required to rearrangement or calibration.

Also, a lot of time is required for setting various reagents, and the reagents may be polluted. Furthermore, since the size of the system is too big, the system includes various independent devices, and thus, information cannot be exchanged with external devices.

SUMMARY

Some example embodiments provide a wide-angle emission filter having uniform filtering characteristics regardless of incident angles.

Some example embodiments provide a wide-angle emission filter including a base matrix, a photoresist, and a colorant. The base matrix has a flat shape and including a transparent material. The base matrix does not generate fluorescent light or phosphorescent light by an excitation light. The photoresist is disposed in the base matrix. The photoresist is fixed in a solid state through at least one method selected from the group consisting of thermal hardening, photo hardening, and drying. The colorant is disposed in the base matrix and includes light having a predetermined wavelength range. The wide-angle emission filter filters the excitation light regardless of an incident angle of the excitation light.

In example embodiments, the wide-angle emission filter may be disposable and used for one time test.

In example embodiments, the photoresist may include a semi-solidified photoresist, which is not completely saturated by light having a short wavelength, and the excitation light may be firstly filtered by the colorant and secondly filtered by the semi-solidified photoresist.

In example embodiments, the photoresist may further include a saturated photoresist disposed in the base matrix, which is completely saturated by the excitation light.

Some example embodiments provide an optical sensor assembly including a wide-angle emission filter and an optical sensor substrate. The wide-angle emission filter is configured to filter an excitation light regardless of an incident angle of the excitation light and to transmit emission light having a wavelength greater than the excitation light. The wide-angle emission filter includes a base matrix, a photoresist, and a colorant. The base matrix has a flat shape and includes a transparent material. The base matrix does not generate fluorescent light or phosphorescent light by the excitation light. The photoresist is disposed in the base matrix. The photoresist is fixed in a solid state through at least one method selected from the group consisting of thermal hardening, photo hardening, and drying. The colorant is disposed in the base matrix and includes light having a predetermined wavelength range. The optical sensor substrate includes a base substrate and an optical sensor array. The base substrate has a flat shape and is integrally formed with the wide-angle emission filter. The optical sensor array includes a plurality of optical sensors buried in an upper portion of the base substrate and arranged in an array shape to sense luminance of the emission light having passed through the wide-angle emission filter.

In example embodiments, the photoresist may include a semi-solidified photoresist, which is not completely saturated by light having a short wavelength, and the excitation light may be firstly filtered by the colorant and secondly filtered by the semi-solidified photoresist.

In example embodiments, the optical sensor substrate may further include a temperature sensor disposed adjacent to the wide-angle emission filter to sense temperature and a first temperature controlling member disposed under the base substrate to control the temperature.

In example embodiments, the optical sensor assembly may further include an interference filter integrally formed on an upper surface of the wide-angle emission filter and being formed by stacking a plurality of refractive layers having different refractive indexes.

In example embodiments, the interference filter may have filtering characteristics of $OD3(10^3)$, at which one thousandth of incident light pass through the interference filter and remaining of the incident light is blocked by the interference filter, but the optical filter assembly may have filtering characteristics of more than or equal to $OD5(10^5)$, at which one hundred thousandth of incident light pass through the optical filter assembly and remaining of the incident light is blocked by the optical filter assembly.

In example embodiments, the interference filter may include a thin film including at least one selected from the group consisting of metal, metal oxide, and nonmetal.

In example embodiments, the optical sensor assembly may further include a second wide-angle emission filter formed on the same plane as the wide-angle emission filter and having a second colorant including a material absorbing light having a wavelength different from a wavelength of the colorant.

Some example embodiments provide a polymerase chain reaction (PCR) system a PCR module and a reader system. The PCR module includes a wide-angle emission filter, an optical sensor substrate, a reaction space, and a first temperature. The wide-angle emission filter is configured to filter an excitation light regardless of an incident angle of the excitation light. The wide-angle emission filter includes a photoresist fixed in a solid state through at least one method selected from the group consisting of thermal hardening, photo hardening, and drying, and a colorant including light having a predetermined wavelength range. The optical sensor substrate includes an optical sensor array including a plurality of optical sensors arranged in an array shape to sense luminance of the emission light having passed through the wide-angle emission filter to generate an optical sensing signal. The reaction space is disposed on the wide-angle emission filter to receive a specimen, in which PCR is performed. The first temperature controlling part receives a temperature control signal to control temperature in the reaction space. The reader system includes a central processing unit, a light source, and a second temperature controlling part. The central processing unit receives the optical sensing signal to calculate an amount of gene amplification based on the optical sensing signal to generate the temperature control signal. The light source generates the excitation light. The second temperature controlling part is connected to the central processing unit to control temperature of the PCR module.

In example embodiments, the PCR module may be detachably combined with the reader system to be used for only one time test.

In example embodiments, the photoresist may include a semi-solidified photoresist, which is not completely saturated by light having a short wavelength, and the excitation light may be firstly filtered by the colorant and secondly filtered by the semi-solidified photoresist.

Some example embodiments provide a method of manufacturing a wide-angle emission filter. The method is provided as follows. An optical sensor substrate including an optical sensor array, which includes a plurality of optical sensors arranged in an array shape to sense luminance of emission light, is formed. Unsolidified photoresist is mixed with a colorant to have fluidity. The mixture of the unsolidified photoresist and the colorant is coated on the optical sensor substrate. The coated mixture of the unsolidified photoresist and the colorant is solidified to generate mixture of the photoresist and the colorant on the optical sensor substrate.

In example embodiments, the photoresist may include a semi-solidified photoresist, which is not completely solidified by light having a short wavelength.

In example embodiments, the coating the mixture of the unsolidified photoresist and the colorant on the optical sensor substrate, may include dropping the mixture of the unsolidified photoresist and the colorant on the optical sensor substrate; and planarizing the dropped mixture of the unsolidified photoresist and the colorant using spin coating.

In example embodiments, the coating the mixture of the unsolidified photoresist and the colorant on the optical sensor substrate, may include printing the mixture of the unsolidified photoresist and the colorant on the optical sensor substrate.

According to the present invention, the semi-solidified photoresist is saturated to be stabilized by the light having the short wavelength such as ultraviolet light, blue light, green light, etc., by absorbing the light having the short wavelength. Thus, the wide-angle emission filter including the semi-solidified photoresist has excellent optical characteristics. That is, in the present invention, the excitation light is firstly blocked by colorant or pigment of the wide-angle emission filter, and is secondly blocked by the semi-solidified photoresist, and thus, the wide-angle emission filter has excellent filtering characteristics in various incident angles. The conventional color filter or the conventional emission filter cannot have the excellent wide-angle filtering characteristics of the present invention.

Also, a complex filter may include the wide-angle emission filter and the interference filter, and thus, an excitation light incident into the interference filter in the vertical direction may be reflected again toward the reaction space. Thus, an amount of the excitation light irradiated into the specimen is increased by twice. Thus, the signal sensed by the optical sensor array is increased by twice, thereby improving sensing accuracy.

Also, when the excitation light is filtered only by an interference filter, an expensive interference filter of OD6 ($10^6$), in which only one millionth of excitation light may pass through the expensive interference filter, is required. However, when the complex filter including the interference filter and the wide-angle emission filter is used, a cheap interference filter of OD2($10^2$) or OD3($10^3$), at which only one hundredth or one thousandth of excitation light may pass through the cheap interference filter, may also be used. The complex filter including the cheap interference filter may have equivalent filtering effect to the expensive interference filter.

Also, the first wide-angle emission filter and the second wide-angle emission filter having different optical characteristics are disposed on the same plane of the optical sensor substrate, and thus, accuracy of the optical sensor array is improved although optical characteristics of the excitation light and the emission light are unknown.

Also, the excitation light is firstly filtered by the semi-solidified photoresist and secondly filtered by the colorant or the pigment, and thus, the wide-angle emission filter has precise cut-off characteristics by the above-mentioned double filtering.

Also, the reaction space, in which the specimen is disposed, is adjacent to the wide-angle emission filter, and thus, quantum efficiency of the optical sensor array is greatly improved.

Also, since the reaction space, in which the specimen is disposed, is adjacent to the wide-angle emission filter, quantum efficiency of the emission light is greatly improved.

Also, the optical part is implanted into the PCR module by the wide-angle emission filter configured to efficiently filter the emission light, and the PCR module is manufactured to be an attachable and detachable module or a disposable module, and thus, a size of the reader system is greatly decreased. Furthermore, the size of the PCR module and the reader system is greatly decreased, and manufacturing cost is decreased.

Also, although the reader system is transported, rearrangement or calibration of relocation of the reader system is unnecessary, and thus, mobility is greatly increased and point-of-care is possible. In particular, detecting systems may be immediately applied to emergency states such as infectious diseases, disaster, identification, etc., thereby minimizing damage.

BRIEF DESCRIPTION OF THE DRAWINGS

Illustrative, non-limiting example embodiments will be more clearly understood from the following detailed description taken in conjunction with the accompanying drawings.

DETAILED DESCRIPTION OF THE EMBODIMENTS

Figure 1:
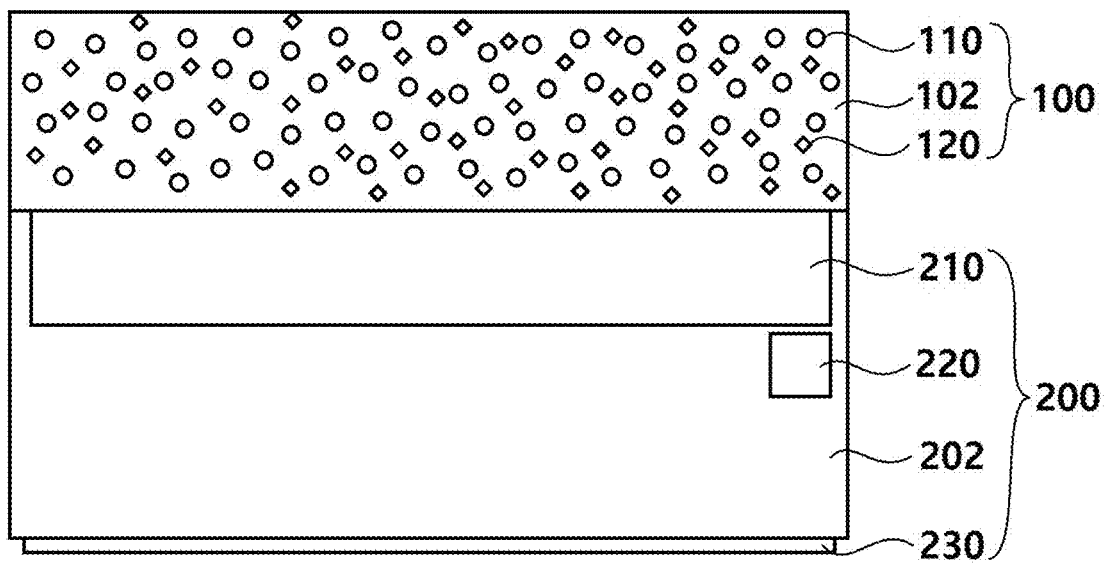
FIG. 1 is a cross-sectional view illustrating a wide-angle emission filter according to one example embodiment of the present invention.

Various example embodiments will be described more fully hereinafter with reference to the accompanying drawings, in which some example embodiments are shown. The present inventive concept may, however, be embodied in many different forms and should not be construed as limited to the example embodiments set forth herein. Rather, these example embodiments are provided so that this disclosure will be thorough and complete, and will fully convey the scope of the present inventive concept to those skilled in the art. In the drawings, the sizes and relative sizes of layers and regions may be exaggerated for clarity. Like numerals refer to like elements throughout.

It will be understood that, although the terms first, second, third etc. may be used herein to describe various elements, these elements should not be limited by these terms. These terms are used to distinguish one element from another. Thus, a first element discussed below could be termed a second element without departing from the teachings of the present inventive concept. As used herein, the term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

The terminology used herein is for the purpose of describing particular example embodiments only and is not intended to be limiting of the present inventive concept. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

'Semi-solidified photoresist' includes photoresist material of a solid state, a semi-solid state, or a gel state, which is not completely saturated by lights having short wavelength such as ultraviolet light, blue light, green light, etc., and is not completely deteriorated or completely saturated by the lights having the short wavelength. The 'semi-solidified photoresist' includes all kinds of photoresist materials in the solid state, a semi-solid state, a gel state, etc., which can absorb the lights having the short wavelength. For example, the 'semi-solidified photoresist' includes a photoresist material solidified by photo-hardening, a photoresist material solidified by thermal hardening, a photoresist material hardened by drying, a photoresist material solidified by multiple hardening of heating, drying, photo-hardening, or a combination thereof, etc.

In the present invention, the semi-solidified photoresist material additionally absorbs the lights (or the excitation light) having the short wavelength such as the ultraviolet light, the blue light, the green light, etc., to be completely saturated, completely solidified, or completely deteriorated. The above-mentioned characteristics, in which the semi-solidified photoresist material is transformed into the completely solidified photoresist and the lights having the short wavelength is absorbed during the transformation, is used for the wide-angle emission filter (or a color filter). Also, light absorbing characteristics of colorant may be used for the wide-angle emission filter (or a color filter).

Hereinafter, embodiments of the present invention will be explained with reference to accompanying drawings. Hereinafter, same elements use the same reference numerals in the drawings, and any repetitive explanations concerning the same elements will be omitted.

FIG. 1 is a cross-sectional view illustrating a wide-angle emission filter according to one example embodiment of the present invention.

Referring to FIG. 1, the optical sensor assembly includes a wide-angle emission filter 100 and an optical sensor substrate 200.

The wide-angle emission filter 100 is integrally formed on the optical sensor substrate 200. The wide-angle emission filter 100 blocks an excitation light generated from a light source 340 (shown in FIG. 3), and transmits an emission light generated from a specimen disposed in a reaction space 240.

The wide-angle emission filter 100 includes a base matrix 102, a semi-solidified photoresist 110, and a colorant 120.

The base matrix 102 is disposed on the optical sensor substrate 200 in a flat shape, and forms an external shape of the wide-angle emission filter 100.

The base matrix 102 may include transparent synthetic resin, glass, metal oxide, etc. In the embodiment of the present invention, the base matrix 102 may include epoxy resin, silicon resin, etc., which does not generate fluorescent light or phosphorescent light and is eco-friendly.

The semi-solidified photoresist 110 is dispersed into the base matrix 102, and includes photoresist fixed in a solid state by thermal-hardening, drying, photo-hardening, etc. For example, the semi-solidified photoresist 110 may include negative photoresist. Alternatively, the semi-solidified photoresist 110 may include positive photoresist.

Although not intended to limit the scope of the present invention by theory, reason for improving excellent optical characteristics of the wide-angle emission filter 100 of the present invention will be explained as follows.

In a conventional color filter, colorant or pigment is fixed in a transparent matrix, and thus, light having a predetermined wavelength is absorbed by the colorant but light having different wavelength transmits the color filter. The photoresist reacts with lights having short wavelengths such as ultraviolet light, blue light, green light, etc., and chemical characteristics and optical characteristics of the photoresist are transformed. When the semi-solidified photoresist 110 is used for a color filter, optical characteristics is changed as time passes. Thus, a thermosetting material having constant optical characteristics, which is not changed although the light having the short wavelength such as the ultraviolet light the blue light, the green light, etc., may be used for the conventional color filter.

However, since the wide-angle emission filter 100 according to the embodiment of the present invention is not used for a long time test device but is used for a disposable test device, the wide-angle emission filter 100 only temporarily maintains optical characteristics during short test period. In particular, when the lights having the short wavelength such as the ultraviolet light, the blue light, the green light, etc., are irradiated onto the semi-solidified photoresist 110, the semi-solidified photoresist 110 absorbs the light having the short wavelength only for short time period, and thus, the semi-solidified photoresist 110 temporarily functions as an excellent optical filter for only a short period and the semi-solidified photoresist 110 loses most of the filtering function by saturation of the semi-solidified photoresist 110 by the lights having the short wavelength. Thus, the semi-solidified photoresist 110 may not be used for the conventional color filter.

In contrast, the semi-solidified photoresist 110 uses the characteristic of absorbing the light having the short wavelength during the semi-solidified photoresist 110 absorbing the lights having the short wavelength, and thus, the wide-angle emission filter 100 having an excellent optical characteristics is used for a disposable testing device. That is, in the present invention, the excitation light is firstly blocked by the colorant 120 and is secondly blocked by the semi-solidified photoresist 110, and thus, the wide-angle emission filter 100 filters incident light regardless of incident angles. The conventional interference filter cannot be used to filter the incident light regardless of the incident angles.

The conventional color filter may also be used to filter the incident light regardless of the incident angles for the disposable testing device, if only the conventional color filter is not completely saturated by the lights having the short wavelength. That is, a new conventional color filter, which is just made and carefully controlled not to be irradiated by the lights having the short wavelength, may also have similar optical characteristics of the semi-solidified photoresist 110. However, in the conventional color filter, the change of optical characteristics during testing is assumed to be a defect. Thus, the semi-solidified photoresist of the conventional color filter is generally removed during calibration of a test device, in order to remove the unstable optical characteristics of an initial stage. However, the wide-angle emission filter 100 of the present invention uses the unstable optical characteristics of the initial stage, because each of the wide-angle emission filters 100 is disposable or throwaway and is used for only one time test.

The colorant 120 may include a material absorbing a predetermined wavelength, for example, a yellow colorant, a red colorant, a blue colorant, a green colorant, etc. In the embodiment of the present invention, the colorant 120 includes a yellow colorant. The yellow colorant may include inorganic colorants or organic colorants. The inorganic colorants of the yellow colorant may include lead chromate, calcium yellow, yellow oxides, complexes inorganic color pigments, bismuth vanadate, etc. The organic colorants of the yellow colorant may include arylamade, diarylide, benzimidazolone, disazo ondensation, organic metal complexes, isoindoline, quinophthalone, anthrapyrimidine, flayanthrone, etc.

Figure 2:
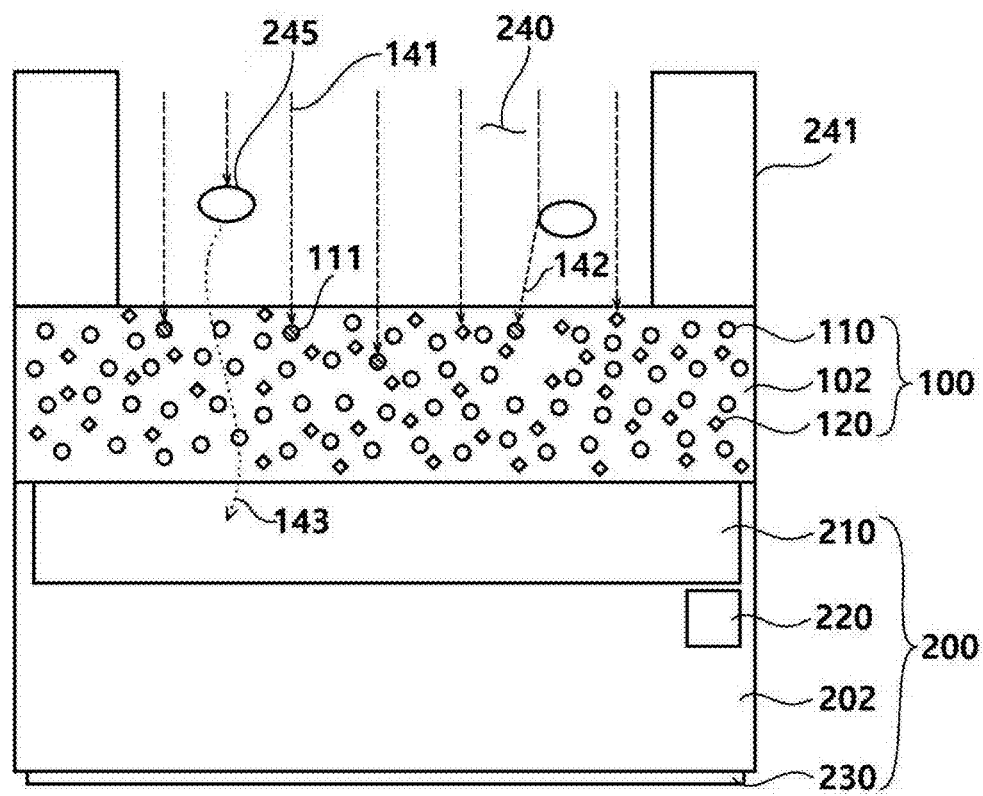
FIG. 2 is a cross-sectional view illustrating a process of filtering light by the wide-angle emission filter shown in FIG. 1.

FIG. 2 is a cross-sectional view illustrating a process of filtering light by the wide-angle emission filter shown in FIG. 1.

Referring to FIGS. 1 and 2, the light generated from a light source 340 (shown in FIG. 3) passes through a light source filter 343 (shown in FIG. 3), and is transformed into an excitation light 141 of a single wavelength. The excitation light 141 of the single wavelength is incident into a reaction space 240 formed between partition walls 241.

A portion of the excitation light 141 incident into the reaction space 240 is irradiated onto a specimen 245, and is transformed into an emission light 143 having greater wavelength and smaller energy. The emission light 143 passes through the wide-angle emission filter 100, and is incident into the optical sensor array 210.

A portion of the excitation light 141 incident into the reaction space 240, which is not incident into the specimen 245 but is incident into the wide-angle emission filter 100, is blocked by the semi-solidified photoresist 110 or the colorant 120, and thus, the portion of the excitation light 141 does not pass through the wide-angle emission filter 100.

In particular, a portion of the excitation light 141 incident into the reaction space 240, which is incident into the wide-angle emission filter 100, may not pass through the wide-angle emission filter 100.

Also, a remaining portion of the excitation light 141 incident into the reaction space 240, which is incident into the wide-angle emission filter 100, is irradiated into the semi-solidified photoresist 110. When the excitation light 141 is irradiated into the semi-solidified photoresist 100, the semi-solidified photoresist 110 may be transformed into a saturated photoresist 111. In the embodiment of the present invention, the optical sensor assembly is manufactured for disposable use, the semi-solidified photoresist 110 of the wide-angle emission filter 100 is sufficient to absorb the excitation light 141 during the disposable test.

Since the semi-solidified photoresist 110 is transformed into the saturated photoresist 111 regardless of incident angles of the excitation light 141, the semi-solidified photoresist 110 may block the excitation light 142 incident into the specimen 245 in various incident angles.

The optical sensor substrate 200 includes a base substrate 202, an optical sensor array 210, a temperature sensor 220, and a first temperature controlling member 230.

The base substrate 202 has a flat shape, and is integrally formed with the wide-angle emission filter 100. The base substrate 202 may include various materials such as silicon, plastic, ceramic, etc.

The optical sensor array 210 is buried into an upper portion of the base substrate 202, so that an upper surface of the base substrate 202 has a flat surface. The optical sensor array 210 has a plurality of optical sensors arranged in an array shape. For example, the optical sensor array 210 may include a plurality of photodiodes, a plurality of thin film transistors, etc.

The optical sensor array 210 is disposed under the wide-angle emission filter 100, and detects luminance of the emission light such as a fluorescent light, a phosphorescent light, etc., which is generated from the specimen 245 in the reaction space 240 (shown in FIG. 2) and passes through the wide-angle emission filter 100. The luminance of the emission light detected by the optical sensor array 210 is transformed into a optical sensing signal, and is output toward a reader system 300 (shown in FIG. 2).

The temperature sensor 220 is disposed adjacent to the wide-angle emission filter 100 to sense temperature in the reaction space 240 (shown in FIG. 2). The temperature sensed by the temperature sensor 220 is transformed into a temperature signal to be output to a first temperature controlling part 270.

The first temperature controlling member 230 is disposed under the base substrate 202 to control a temperature in the reaction space 240 (shown in FIG. 2) by the control of the first temperature controlling part 270. In the embodiment of the present invention, the first temperature controlling member 230 may include a heater, a thermoelectric element, etc.

Alternatively, the first temperature controlling member 230 may be disposed on an upper portion of the wide-angle emission filter 100, inside of the reaction space 240, a side surface of the reaction space 240, an upper portion of the reaction space 240, etc.

Figure 3:
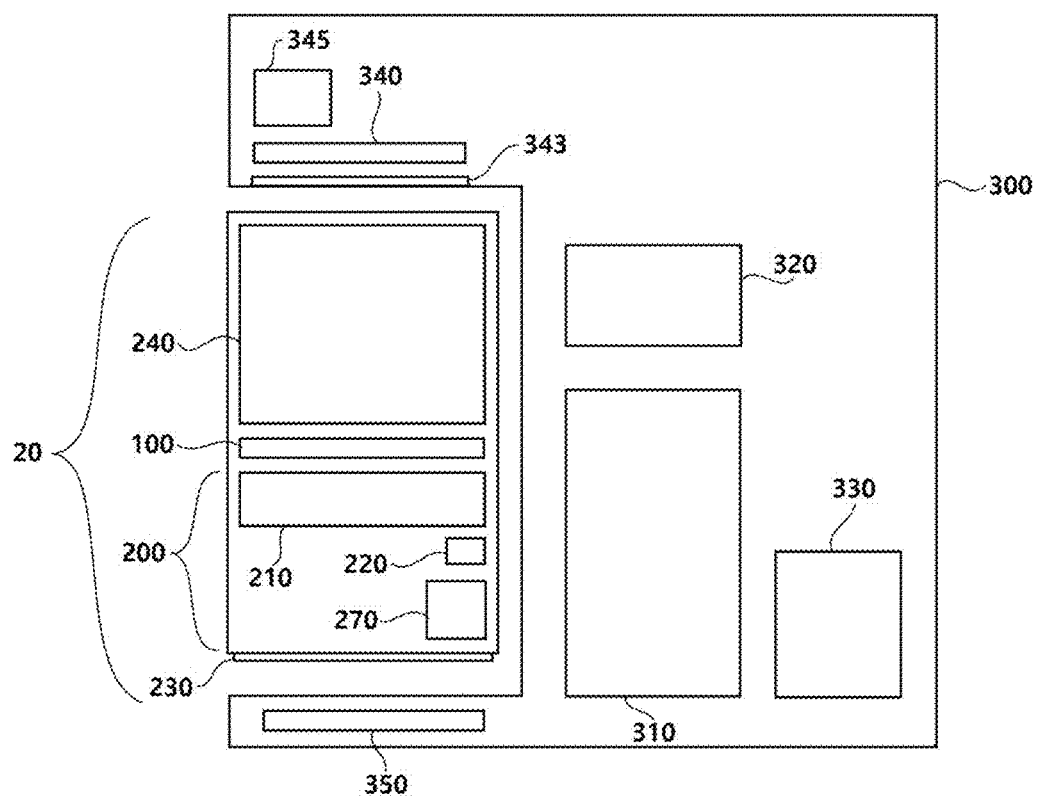
FIG. 3 is a block diagram illustrating a PCR system including the optical sensor assembly shown in FIG. 1.

FIG. 3 is a block diagram illustrating a PCR system including the optical sensor assembly shown in FIG. 1.

Referring to FIGS. 1 and 3, the PCR system includes a PCR module 20 and a reader system 300.

The PCR module 20 includes the wide-angle emission filter 100, the optical sensor substrate 200, the reaction space 240, and the first temperature controlling part 270.

The wide-angle emission filter 100 and the optical sensor substrate 200 are explained with reference to FIG. 1, and thus, any repetitive explanations concerning the above-elements will be omitted.

The reaction space 240 is disposed on the wide-angle emission filter 100, and receives the specimen 245. The PCR process is performed in the reaction space 240. A plurality of partition walls are protruded from the wide-angle emission filter 100 in a vertical direction to form the reaction space 240. For example, a plurality of reaction spaces having small sizes of 80 μm to 3 mm may be formed by the partition walls.

The first temperature controlling part 270 controls the first temperature controlling member 230 by a signal received from the reader system 300 to control the temperature in the reaction space 240.

The reader system 300 includes a central processing unit 210, a memory 320, an interface 330, a light source 340, an optical filter 343, a light source driving circuit 345, a second temperature controlling part 350. In the embodiment of the present invention, the PCR module 200 is detachable combined with the reader system 300, and is disposable after one time experiment.

The central processing unit 310 reads driving data stored in the memory 320 to drive the second temperature controlling part 350 and the PCR module 20. The central processing unit 310 receives optical sensing signal, temperature information, etc., from the PCR module 20 to store the received information in the memory 320 in real-time. The central processing unit 310 calculates an amount of gene amplification based on the optical sensing signal, the temperature information, etc., from the PCR module 20 in real-time to generate gene amplification information. The central processing unit 310 stores the gene amplification information in the memory 320 in real time, and transmits the gene amplification information to the interface 330.

The memory 320 is connected to the central processing unit 310, and drives the second temperature controlling part 350 and the PCR module 20 using pre-stored driving data, and stores the optical sensing signal, the temperature information, etc., in real time. The driving data may include temperature control data, photo control data, etc., and may be stored in the memory 320 as a data format, or may be input from the outside through an input device (not shown). For example, the memory 320 may include various memory devices such as DDR3, SRAM(Frame), SSD(FLASH), etc.

The interface 330 is connected to the central processing unit 310 to transmit the gene amplification information received from the central processing unit 310 in real-time to the outside or to transmit external input signal to the central processing unit 310. In the embodiment of the present invention, the interface 330 may include a communication interface (not shown), a data interface (not shown), a display device (not shown), an input device (not shown), an output device (not shown), etc. The communication interface (not shown) may include a wireless LAN (Wlan), a WiFi, a Bluetooth, etc. The data interface (not shown) may include a Universal Serial Bus (USB), an Inter-Integrated Circuit ($I^2C$), a Universal Asynchronous Receiver/Transmitter (UART), a Pulse Width Modulation (PWM), a Low Voltage Differential Signaling (LVDS), a Mobile Industry Processor Interface (MIPI), etc. The display device (not shown) may include a Liquid Crystal Display (LCD), Organic a Light Emitting Display (OLED), a Cathode Ray Tube (CRT), etc. The input device (not shown) may include a mouse, a keyboard, etc. The output device (not shown) may include a printer, a facsimile, etc.

The light source 340 generates excitation light using a light source driving signal.

The optical filter 343 is disposed under the light source 340, and filters the excitation light generated from the light source 340 to transmit only some light having a predetermined wavelength range. In the embodiment of the present invention, the optical filter 343 minimizes noise caused by an external light and decreases error of the optical sensor array 210, which may caused by luminance changed by the external light.

The light source driving circuit 345 drives the light source 340 using the light source driving signal received from the central processing unit 310.

The second temperature controlling part 350 is connected to the central processing unit 310 to control the temperature of the PCR module 20 using the temperature control data received from the central processing unit 310.

FIGS. 4 to 7 are cross-sectional views illustrating a method of manufacturing the wide-angle emission filter shown in FIG. 1.

Figure 4:
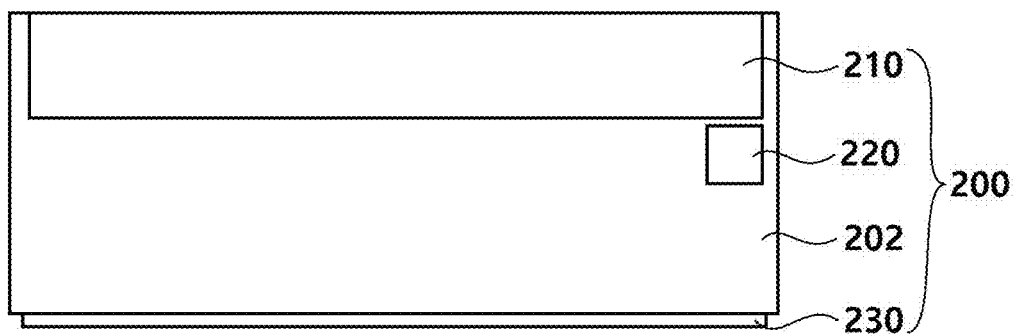
FIGS. 4 to 7 are cross-sectional views illustrating a method of manufacturing the wide-angle emission filter shown in FIG. 1.

FIG. 4 is a cross-sectional view illustrating forming the optical sensor substrate in order to manufacture the wide-angle emission filter of the embodiment of the present invention.

Referring to FIG. 4, firstly, the optical sensor array 210 and the temperature sensor 220 is formed in the base substrate 202.

The first temperature controlling member 230 is then formed on a lower surface of the base substrate 202.

Figure 5:
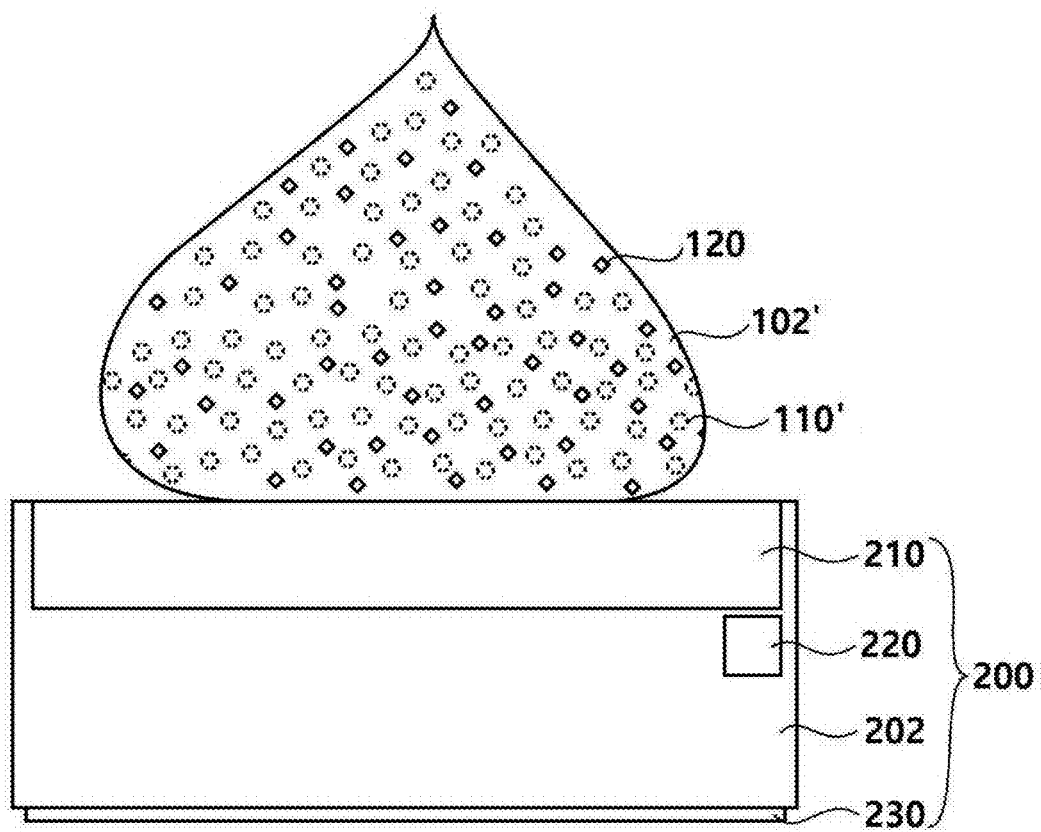

FIG. 5 is a cross-sectional view illustrating dropping a mixture of unsolidified base matrix, unsolidified photoresist, and colorant on the optical sensor substrate shown in FIG. 4.

Referring to FIG. 5, the unsolidified base matrix 102', the unsolidified photoresist 110', and the colorant 120 are then mixed. The mixture of the undolidified base matrix 102', the unsolidified photoresist 110', and the colorant 120 has fluidity.

The mixture of the unsolidified base matrix 102', the unsolidified photoresist 110, and the colorant 120 are then dropped on the optical sensor substrate 200. In another embodiment, the mixture of the unsolidified base matrix 102', the unsolidified photoresist 110, and the colorant 120 may be printed on the optical sensor substrate 200.

The dropped mixture of the unsolidified base matrix 102', the unsolidified photoresist 110, and the colorant 120 is then planarized. In the embodiment of the present invention, the dropped mixture of the the unsolidified base matrix 102', the unsolidified photoresist 110, and the colorant 120 may be planarized by spin coating. In another embodiment of the present invention, the dropped mixture of the the unsolidified base matrix 102', the unsolidified photoresist 110, and the colorant 120 may be planarized by various planarizing methods such as printing, rolling by a roller, etc.

Figure 6:
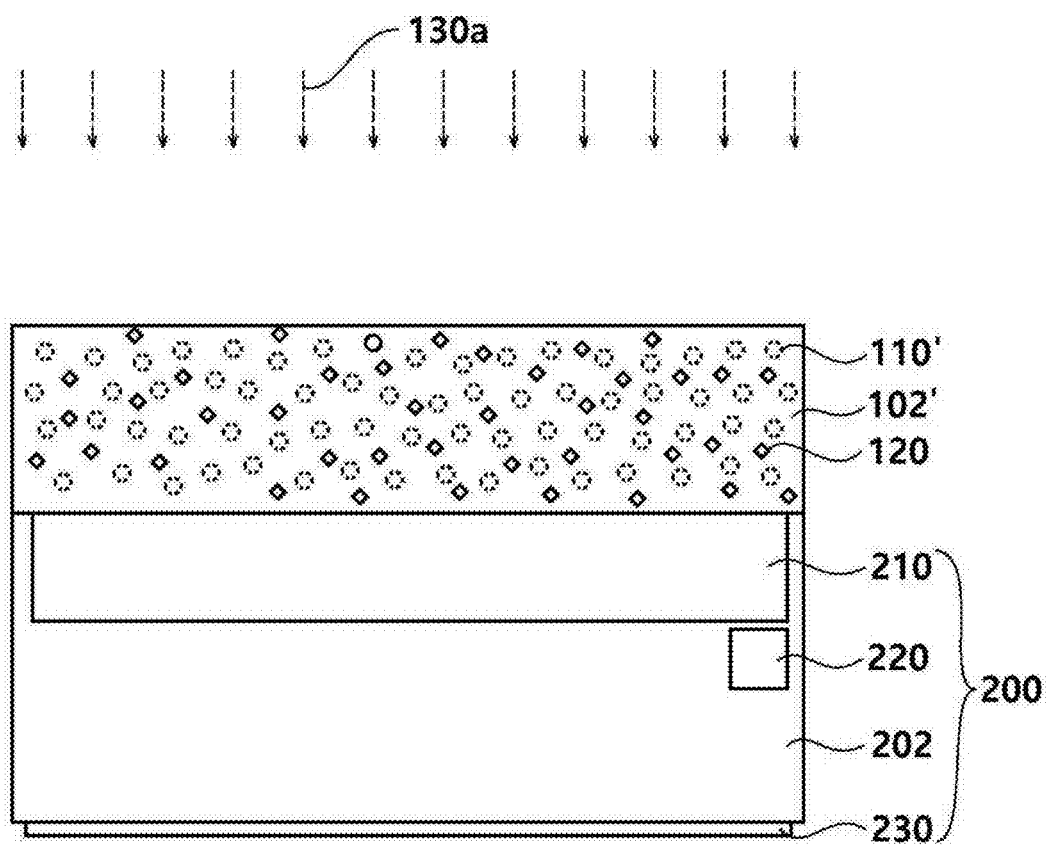

FIG. 6 is a cross-sectional view illustrating solidifying the mixture of the unsolidified base matrix, the unsolidified photoresist, and the colorant shown in FIG. 5.

Referring to FIG. 6, photo hardening 130a is performed on the planarized mixture of the unsolidified base matrix 102', the unsolidified photoresist 110', and the colorant 120.

Figure 7:
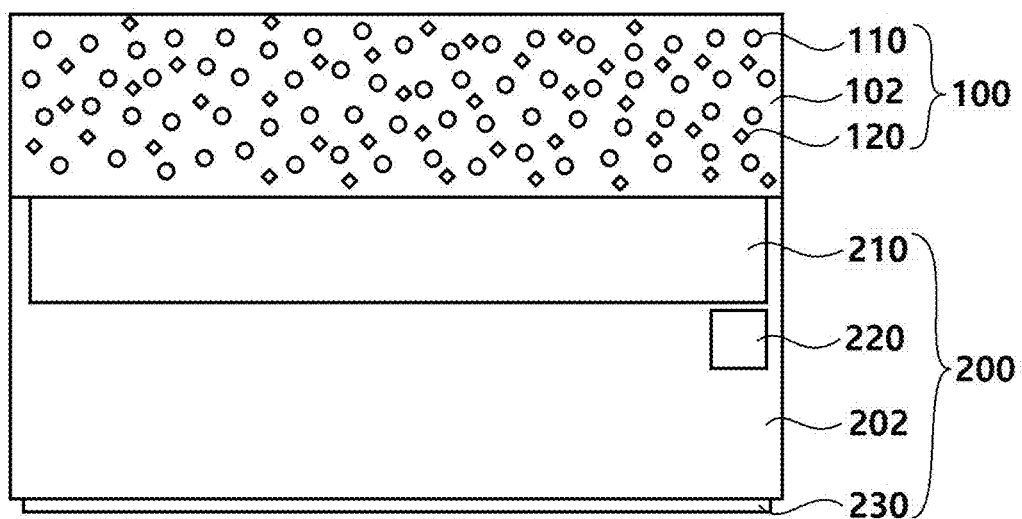

FIG. 7 is a cross-sectional view illustrating solidifying the planarized misture of the unsolidified base matrix, the unsolidified photoresist, and the colorant shown in FIG. 6 to form semi-solidified base matrix, semi-solidified photoresist, and colorant.

Referring to FIG. 7, when the photo hardening 130a is performed on the planarized mixture of the unsolidified base matrix 102', the unsolidified photoresist 110', and the colorant 120, the planarized mixture of the unsolidified base matrix 102', the unsolidified photoresist 110', and the colorant 120 is changed into the semi-solidified base matrix 102, the semi-solidified photoresist 110, and the colorant 120.

Thus, the wide-angle emission filter 100 including the semi-solidified base matrix 102, the semi-solidified photoresist 110, and the colorant 120 is formed on the optical sensor substrate 200.

Figure 8:
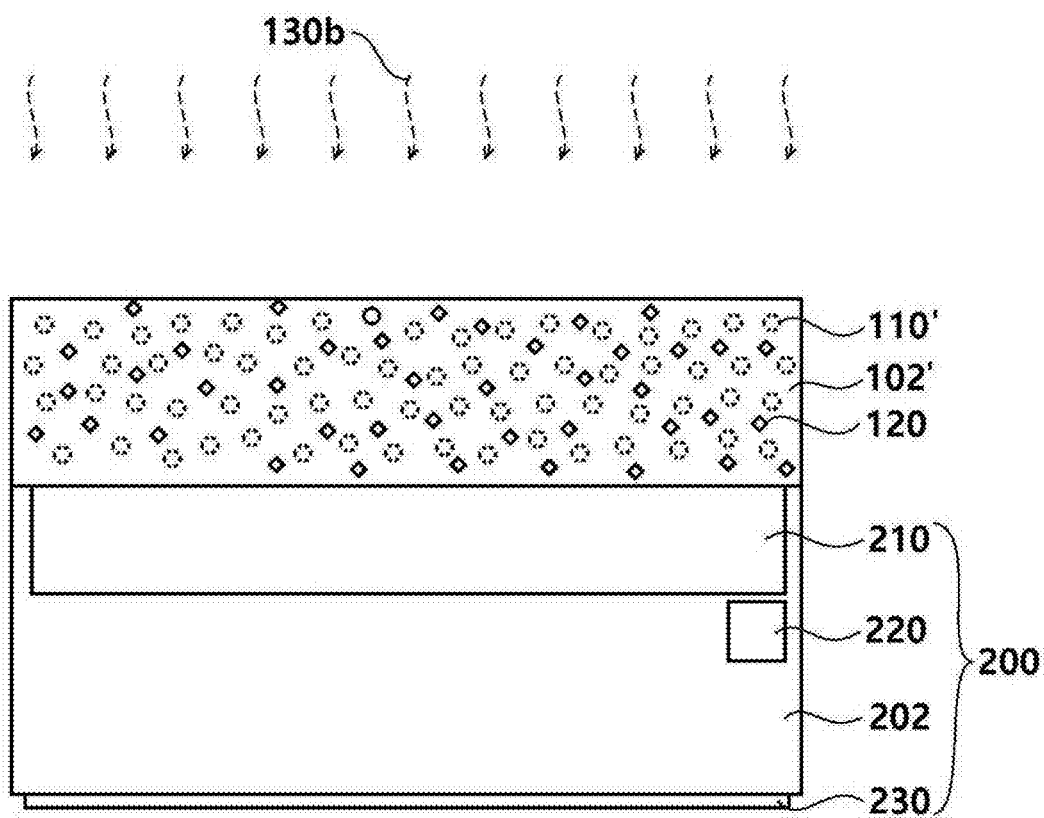
FIG. 8 is a cross-sectional view illustrating a method of manufacturing a wide-angle emission filter according to another embodiment of the present invention.

FIG. 8 is a cross-sectional view illustrating a method of manufacturing a wide-angle emission filter according to another embodiment of the present invention. The wide-angle emission filter of FIG. 8 is substantially the same as shown in FIGS. 1 to 7 except the planarized mixture of the base matrix, the unsolidified photoresist, and the colorant is thermally hardened to form the semi-solidified base matrix, the semi-solidified photoresist, and the colorant. Thus, any repetitive explanations concerning the same elements will be omitted.

Referring to FIGS. 1 to 5, and FIG. 8, the thermal hardening 130b is performed to a planarized mixture of the unsolidified base matrix 102', the unsolidified photoresist 110', and the colorant 120.

Referring to FIG. 8, when the thermal hardening 130b is applied to the planarized mixture of the unsolidified base matrix 102', the unsolidified photoresist 110', and the colorant 120, the planarized mixture of the unsolidified base matrix 102', the unsolidified photoresist 110', and the colorant 120 is transformed into the semi-solidified base matrix 102, the semi-solidified photoresist 110, and the colorant 120.

Figure 9:
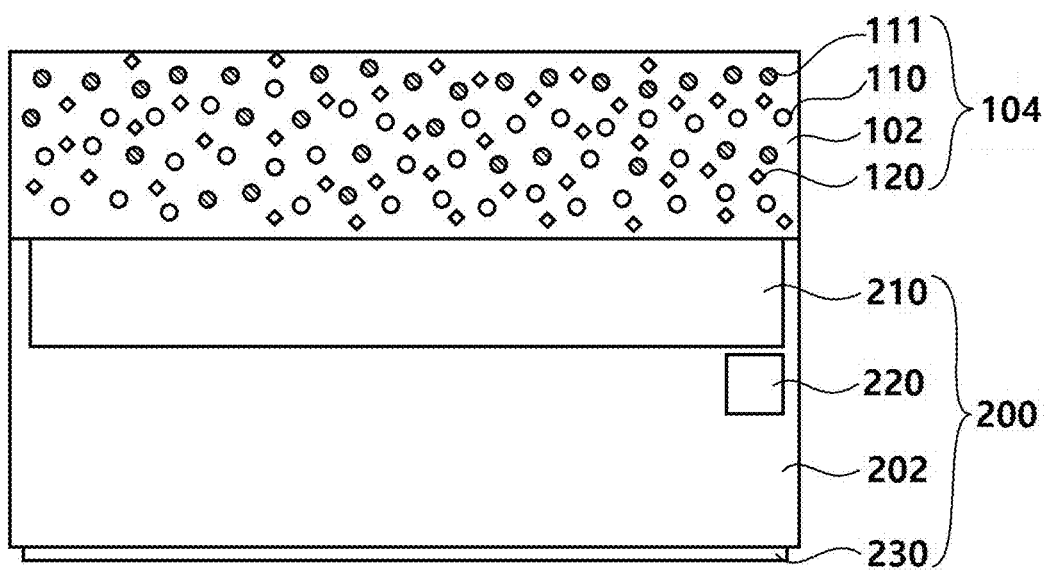
FIG. 9 is a cross-sectional view illustrating a wide-angle emission filter according to another embodiment of the present invention.

FIG. 9 is a cross-sectional view illustrating a wide-angle emission filter according to another embodiment of the present invention. The wide-angle emission filter of FIG. 9 is substantially the same as shown in FIGS. 1 to 7 except a solidified photoresist, and the colorant is thermally hardened to form the semi-solidified base matrix, the semi-solidified photoresist, and the colorant. Thus, any repetitive explanations concerning the same elements will be omitted.

Referring to FIG. 9, the wide-angle emission filter 104 is disposed on an optical sensor substrate 200.

The wide-angle emission filter 104 includes a base matrix 102, a semi-solidified photoresist 110, a saturated photoresist 111, and colorant 120.

The saturated photoresist 111 is formed by irradiating lights having a short wavelength such as ultraviolet light, blue light, green light, etc., onto a semi-solidified photoresist 110. In another embodiment of the present invention, the saturated photoresist 111 may be formed by irradiating the blue light, the green light, etc., onto the semi-solidified photoresist 110.

A ratio of the semi-solidified photoresist 110 and the saturated photoresist 111 is not limited. When the semi-solidified photoresist 110 of enough amount to absorb an excitation light is included in the wide-angle emission filter, only small amount of the semi-solidified photoresist 110 may exist in the wide-angle emission filter. In the present invention, the wide-angle emission filter 104 is used in a disposable test, and thus, the ratio of the semi-solidified photoresist 110 and the saturated photoresist 111 may be equal to or less than 1:1,000. For example, the ratio of the semi-solidified photoresist 110 and the saturated photoresist 111 may be 1:1,000,000 to 1:10.

Figure 10:
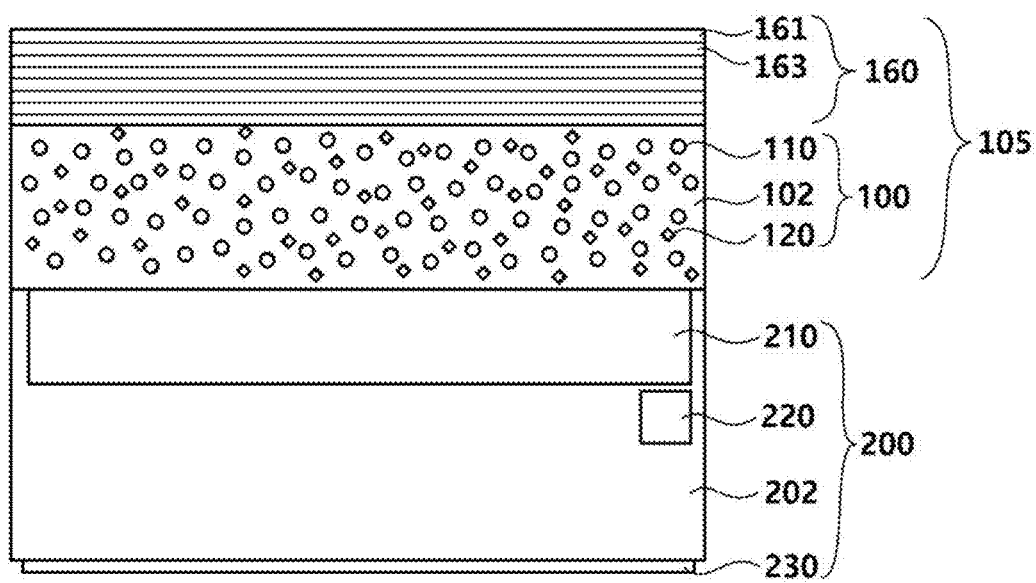
FIG. 10 is a cross-sectional view illustrating an optical filter assembly according to another embodiment of the present invention.

FIG. 10 is a cross-sectional view illustrating an optical filter assembly according to another embodiment of the present invention. The optical filter assembly of FIG. 10 is substantially the same as shown in FIGS. 1 to 9 except an interference filter. Thus, any repetitive explanations concerning the same elements will be omitted.

Referring to FIG. 10, the optical filter assembly 105 includes a wide-angle emission filter 100 and the interference filter 160.

The interference filter 160 is integrally formed with the wide-angle emission filter 100, and is formed by stacking a plurality of refractive layers 161 and 163 having different refractive indexes. For example, the interference filter 160 may include a plurality of first refractive layers 161 and a plurality of second refractive layers 163. When the excitation light is filtered only by an interference filter, the interference filter requires high performance of $OD6(10^6)$, in which only one millionth of excitation light may pass through the expensive interference filter. However, when the interference filter 160 is combined with the wide-angle emission filter 100, the interference filter 160 requires only $OD2(10^2)$ or $OD3(10^3)$, at which only one hundredth or one thousandth of excitation light may pass through the cheap interference filter, and the optical filter assembly 105 may perform substantially equal to or more performance than the only interference filter of $OD6(10^6)$.

Thus, manufacturing cost of the optical filter assembly 105 (or a complex filter) may be decreased.

The interference filter 160 reflects the excitation light 141 (shown in FIG. 2) toward a reaction space 240 (shown in FIG. 2), and is not incident into the wide-angle emission filter 100. The reflected excitation light reflected toward the reaction space 240 (shown in FIG. 2) is incident into a specimen 245 (shown in FIG. 2) again, and thus, an amount of the excitation light irradiated onto the specimen 245 (shown in FIG. 2) is increased by twice. When the amount of the excitation light irradiated onto the specimen 245 (shown in FIG. 2) is increased by twice, the amount of emission light 143, which is a fluorescent light or a phosphorescent light generated from the specimen 245 (shown in FIG. 2), is also increased by twice. When the amount of the emission light 143 is increased by twice, intensity of signal sensed by an optical sensor array 210 is also increased by twice, thereby improving sensing accuracy.

An excitation light 142 (shown in FIG. 2) incident into the interference filter 160 in an inclined direction passes through the interference filter 160, and is irradiated onto the wide-angle emission filter 100.

The excitation light 142 (shown in FIG. 2) irradiated onto the wide-angle emission filter 100 is blocked by the semi-solidified photoresist 110 or the colorant 120, and is not irradiated onto the optical sensor array 210.

According to the embodiment of the present invention, the excitation light 141 (shown in FIG. 2) incident into the interference filter 160 in the vertical direction may be reflected again toward the reaction space 240 (shown in FIG. 2). Thus, an amount of the excitation light irradiated into the specimen 245 (shown in FIG. 2) is increased by twice. Thus, the signal sensed by the optical sensor array 210 is increased by twice, thereby improving sensing accuracy.

Figure 11:
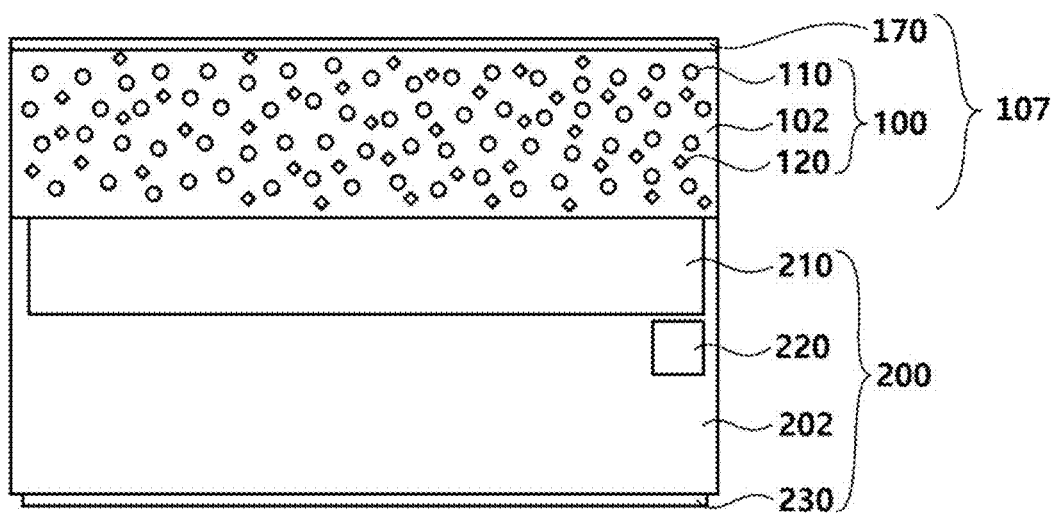
FIG. 11 is a cross-sectional view illustrating an optical filter assembly according to another embodiment of the present invention.

FIG. 11 is a cross-sectional view illustrating an optical filter assembly according to another embodiment of the present invention. The optical filter assembly of FIG. 11 is substantially the same as shown in FIG. 10 except an interference filter. Thus, any repetitive explanations concerning the same elements will be omitted.

Referring to FIG. 11, the optical filter assembly 105 includes a wide-angle emission filter 100 and an interference filter 170.

In the embodiment of the present invention, the interference filter 170 includes a thin film of metal, metal oxide, or nonmetal. For example, the interference filter 170 may include a silver thin film, a zinc sulfide (blende), a magnesium fluoride layer, a silicon oxide (SiO2) layer, a titanium oxide (TiO$_2$) layer, etc.

Figure 12:
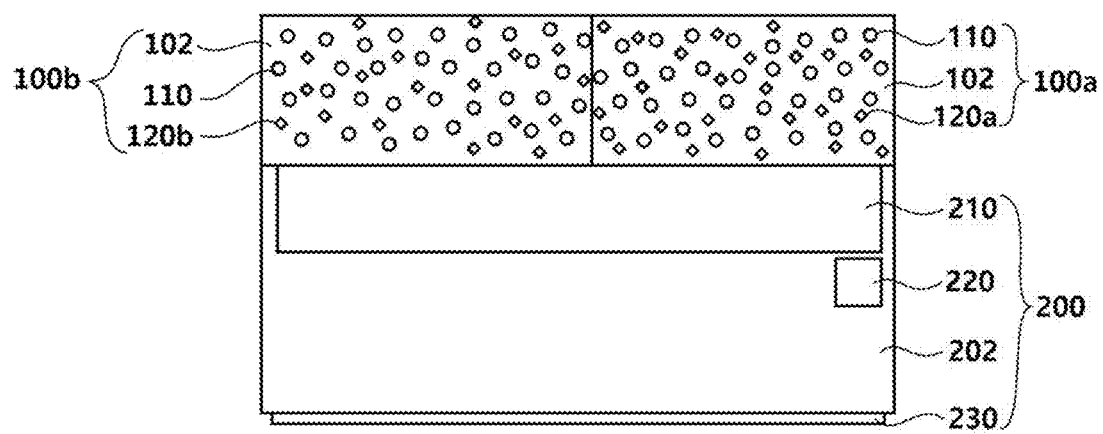
FIG. 12 is a cross-sectional view illustrating an optical filter assembly according to another embodiment of the present invention.

FIG. 12 is a cross-sectional view illustrating an optical filter assembly according to another embodiment of the present invention. The optical filter assembly of FIG. 12 is substantially the same as shown in FIGS. 1 to 7 except a first wide-angle emission filter and a second wide-angle emission filter. Thus, any repetitive explanations concerning the same elements will be omitted.

Referring to FIG. 12, the optical sensor assembly includes a first wide-angle emission filter 100a, a second wide-angle emission filter 100b, and an optical sensor substrate 200.

The first wide-angle emission filter 100a includes a base matrix 102, a semi-solidified photoresist 110, and a first colorant 120a.

The first colorant 120a absorbs light having a predetermined wavelength range. Examples for the first colorant 120a may include yellow colorant, red colorant, blue colorant, green colorant, etc. In the embodiment of the present invention, the first colorant 120a may include the yellow colorant.

The secondwide-angle emission filter 100b includes a base matrix 102, a semi-solidified photoresist 110, and a second colorant 120b.

The second colorant 120b absorbs light having a wavelength range different from that of the first colorant 120a. In the embodiment of the present invention, the second colorant 120b may include the green colorant.

The first wide-angle emission filter 100a and the second wide-angle emission filter 100b are integrally formed on the same plane of the optical sensor substrate 200.

Referring again to FIGS. 2, 3 and 12, the first wide-angle emission filter 100a and the second wide-angle emission filter 100b include the first colorant 120a and the second colorant 120b, which absorb lights having different wavelength ranges.

When the wide-angle emission filter includes only one colorant, the colorant should correspond to optical characteristics of excitation light and emission light. However, in the embodiment of the present invention, the first and second wide-angle emission filters 100a and 100b include the first and second colorants 120a and 120b having different wavelength ranges, and thus, sensing accuracy is improved although precise optical characteristics of excitation light 141 generated from a light source 340, excitation light 142 scattered by a specimen 245 are unknown.

For example, when a wavelength range of a green light is interposed between a wavelength range of the excitation lights 141 and 142 and a wavelength range of the emission light 143, the optical sensor array 210 disposed under the second wide-angle emission filter 100b may differentiate and sense the emission light 143 from the excitation lights 141 and 142. However, when a wavelength range of a yellow light is interposed between a wavelength range of the excitation lights 141 and 142 and a wavelength range of the emission light 143, the optical sensor array 210 disposed under the first wide-angle emission filter 100a may differentiate and sense the emission light 143 from the excitation lights 141 and 142.

In FIG. 12, although only two wide-angle emission filters 100a and 100b having two different optical characteristics are disclosed, those skilled in the art will readily appreciate that many modifications are possible in the example embodiments without materially departing from the novel teachings and advantages of the present inventive concept. For example, three of more wide-angle emission filters having three or more different optical characteristics may be disposed on the same plane of the optical sensor substrate 200.

According to the embodiment of the present invention, the first wide-angle emission filter 100a and the second wide-angle emission filter 100b having different optical characteristics are disposed on the same plane of the optical sensor substrate 200, and thus, accuracy of the optical sensor array is improved although optical characteristics of the excitation lights 141 and 142 and the emission light 143 are unknown.

Table 1 represents optical characteristics of various fluorescent materials used for disposable test. In Table 1, fluorescent materials are used for indicating PCR, immune test, disease test, etc. When lights having excitation light wavelengths are irradiated onto the fluorescent materials, the fluorescent materials generates light having emission light wavelengths. LWP represents a wavelength of a long wavelength pass filter. When the excitation light of a high energy is irradiated onto the fluorescent material, the fluorescent material becomes an excited state, and then, becomes a ground state, thereby generating a fluorescent light of a low energy as the emission light. Since a wavelength of a light is decreased as an energy of the light is increased, a wavelength of the excitation light having the high energy is smaller than a wavelength of the emission light having the low energy.

TABLE 1

| | Fluorescent Materials | Excitation Light Wavelength, nm | Emission Light Wavelength, nm | Wide-Angle Emission Filter, nm |
|---|---|---|---|---|
| 1 | FAM | 494 | 520 | LWP 510 |
| 2 | HEX | 535 | 556 | LWP 535 |
| 3 | ROX | 575 | 605 | LWP 595 |
| 4 | CY5 | 646 | 662 | LWP 650 |
| 5 | CY5.5 | 683 | 707 | LWP 695 |

Referring to Table 1, when the fluorescent material was FAM, the excitation light had a maximum intensity at a wavelength of 494 nm, and the emission light had a maximum intensity at a wavelength of 520 nm. A wide-angle emission filter of LWP510 blocked light having a wavelength smaller than 510 nm and transmitted light having a wavelength greater than 510 nm. Thus, the emission light generated from FAM passed through the wide-angle emission filter of LWP510.

When the fluorescent material was HEX, the excitation light had a maximum intensity at a wavelength of 556 nm, and the emission light had a maximum intensity at a wavelength of 556 nm. A wide-angle emission filter of LWP 545 blocked light having a wavelength smaller than 545 nm and transmitted light having a wavelength greater than 545 nm. Thus, the emission light generated from HEX passed through the wide-angle emission filter of LWP545.

When the fluorescent material was ROX, the excitation light had a maximum intensity at a wavelength of 575 nm, and the emission light had a maximum intensity at a wavelength of 605 nm. A wide-angle emission filter of LWP595 blocked light having a wavelength smaller than 595 nm and transmitted light having a wavelength greater than 595 nm. Thus, the emission light generated from ROX passed through the wide-angle emission filter of LWP595.

When the fluorescent material was CY5, the excitation light had a maximum intensity at a wavelength of 646 nm, and the emission light had a maximum intensity at a wavelength of 662 nm. A wide-angle emission filter of LWP650 blocked light having a wavelength smaller than 650 nm and transmitted light having a wavelength greater than 650 nm. Thus, the emission light generated from CY5 passed through the wide-angle emission filter of LWP650.

When the fluorescent material was CY5.5, the excitation light had a maximum intensity at a wavelength of 683 nm, and the emission light had a maximum intensity at a wavelength of 707 nm. A wide-angle emission filter of LWP695 blocked light having a wavelength smaller than 695 nm and transmitted light having a wavelength greater than 695 nm. Thus, the emission light generated from CY5.5 passed through the wide-angle emission filter of LWP695.

Figure 13:
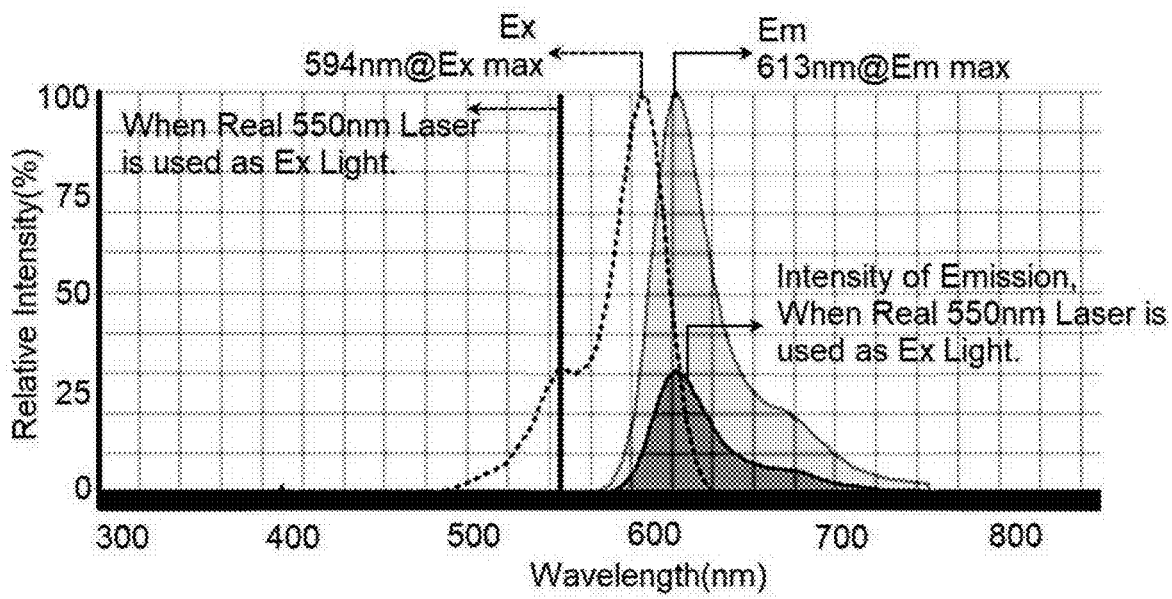
FIG. 13 is a graph illustrating emission light and excitation light according to one embodiment of the present invention.

FIG. 13 is a graph illustrating emission light and excitation light according to one embodiment of the present invention.

Referring to FIG. 13, when excitation light having a maximum intensity at a wavelength of 594 nm was irradiated onto Texas Red fluorescent material, fluorescent light having a maximum intensity at a wavelength of 613 nm was emitted. When excitation light having a maximum intensity at a wavelength of 550 nm was irradiated onto Texas Red fluorescent material, fluorescent light having the same maximum intensity as the wavelength of 613 nm was emitted. The fluorescent light had the same maximum intensity at the wavelength of 613 nm although the lights having maximum intensities at the different wavelengths of 594 nm and 550 nm were irradiated. However, the intensity of the emission light generated from the excitation light having the maximum intensity at the wavelength of 550 nm was smaller than the intensity of the emission light generated from the excitation light having the maximum intensity at the wavelength of 594 nm.

Figure 14:
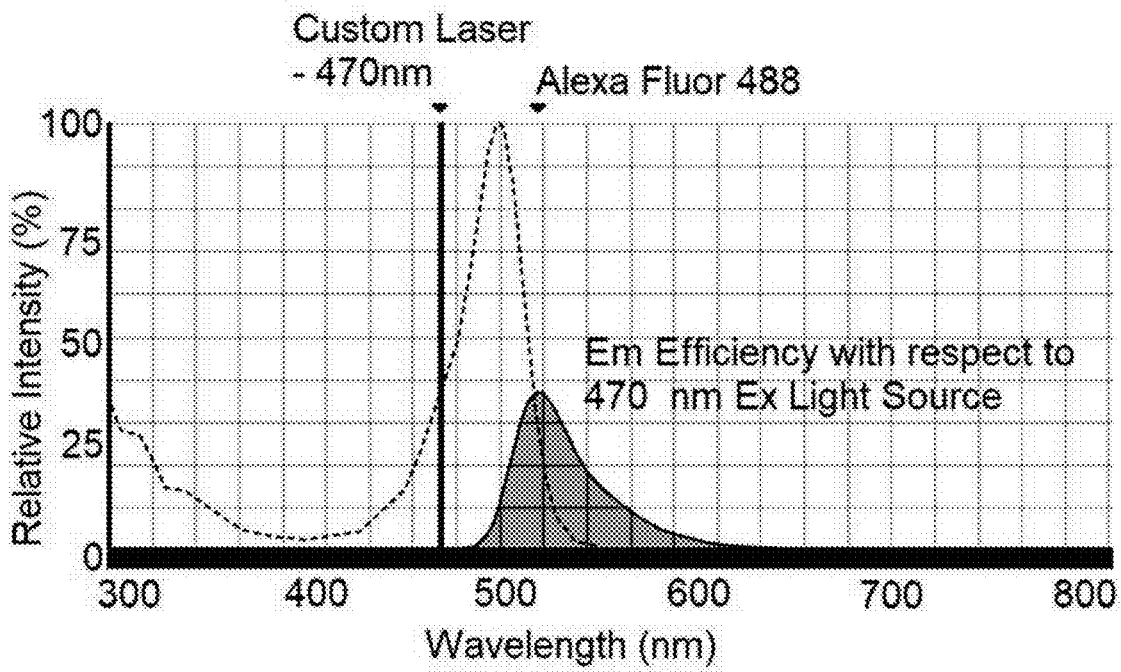
FIGS. 14 and 15 are graphs illustrating optical characteristics of a wide-angle emission filter according to one embodiment of the present invention.
Figure 15:
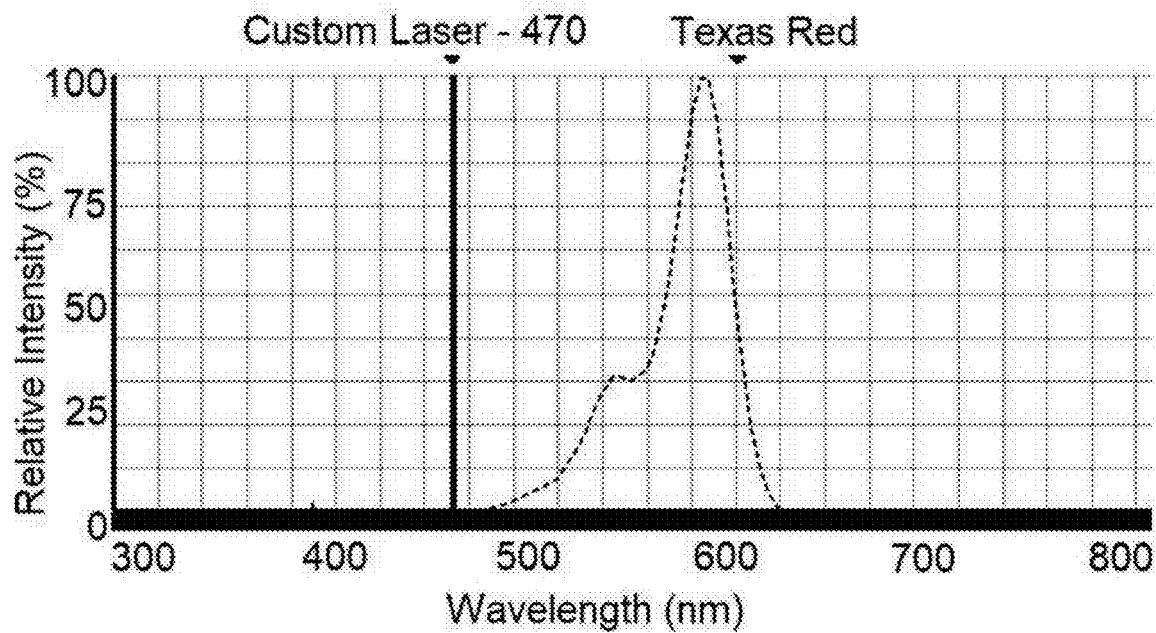

FIGS. 14 and 15 are graphs illustrating optical characteristics of a wide-angle emission filter according to one embodiment of the present invention. In particular, FIGS. 14 and 15 illustrate intensities of emission lights based on wavelengths of incident excitation lights.

FIG. 14 is a graph illustrating optical characteristics of emitted light generated by irradiating laser having a wavelength of 470 nm onto Alexa Flour 488 fluorescent material. When excitation light having a wavelength of 494 nm was irradiated onto Alexa Flour 488, amount of emission light having a maximum intensity at a wavelength of 520 nm was maximum. That is, when the excitation light having the wavelength of 494 nm was irradiated onto Alexa Flour 488, the intensity of the emission light was maximum. When the excitation light having wavelengths different from 494 nm was irradiated, the intensity of the emission light was decreased or eliminated.

When the laser having the wavelength of 470 nm was irradiated onto Alex Flour 488, the intensity of the emission light was decreased by about 40% compared with the intensity of the emission light generated by the laser having the wavelength of 494 nm. The emission light generated from Alex Flour 488 had a maximum intensity at a wavelength of 530 nm.

FIG. 15 is a graph illustrating optical characteristics of emitted light generated by irradiating laser having a wavelength of 470 nm onto Texas Red fluorescent material.

The wavelength of 470 nm was disposed outside of the graph illustrating the optical characteristics of Texas Red fluorescent material, and thus, Texas Red fluorescent material was not excited by the laser having the wavelength of 470 nm. Thus, fluorescent light was not emitted.

When intensity of a fluorescent light emitted from a fluorescent material was increased, sensing efficiency of an optical sensor was improved. Thus, excitation light is preferably to have a wavelength corresponding to maximum intensity of each fluorescent material. However, since the wavelength corresponding to the maximum intensity of each fluorescent material is similar to a wavelength of emitted fluorescent light, sensing emission light requires precise cut-off characteristics of an emission filter. In particular, since the intensity of the emission light is very smaller than the intensity of the excitation light, sensing the emission light may be nearly impossible by a small amount of the excitation light having passed through the emission filter.

Referring again to FIG. 2, the wide-angle emission filter 100 of the present invention firstly filters the excitation lights 141 and 142 by the colorant 120, and secondly filters the excitation lights 141 and 142 by the semi-solidified photoresist 110. Thus, the wide-angle emission filter 100 has precise cut-off characteristics by the first and second filterings.

In the embodiment of the present invention, the cut-off characteristics of the wide-angle emission filter 100 is determined by kinds of colorants 120. In the embodiment of the present invention, the colorant 120 may include yellow colorant. In another embodiment of the present invention, the colorant 120 may include yellow colorant, green colorant, red colorant, blue colorant, or a combination thereof.

Figure 16:
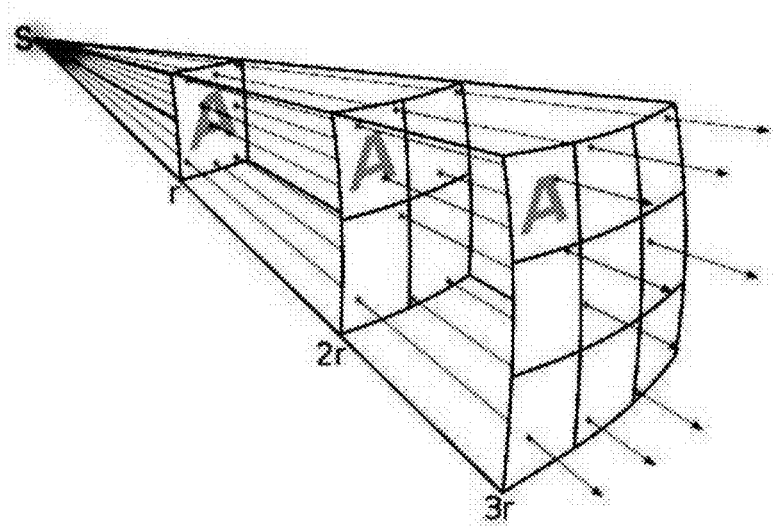
FIG. 16 is a perspective view illustrating optical characteristics of emission light according to one embodiment of the present invention.

FIG. 16 is a perspective view illustrating optical characteristics of emission light according to one embodiment of the present invention.

Referring to FIG. 16, intensity of emission light, that is, quantum efficiency, is reversely proportional to a distance from a light source of the emission light.

$$\text{intensity} \propto \frac{1}{\text{distance}^2} \qquad \text{[Equation 1]}$$

Referring again to FIGS. 2 and 3, since a reaction space 240, in which a specimen 245 is disposed, is disposed adjacent to a wide-angle emission filter, a distance between the specimen 245, which is a light source of emission light 143, and an optical sensor array 210 is very close. When the distance between the specimen 245 and the optical sensor array 210 is very close, quantum efficiency is highly increased.

Figure 17:
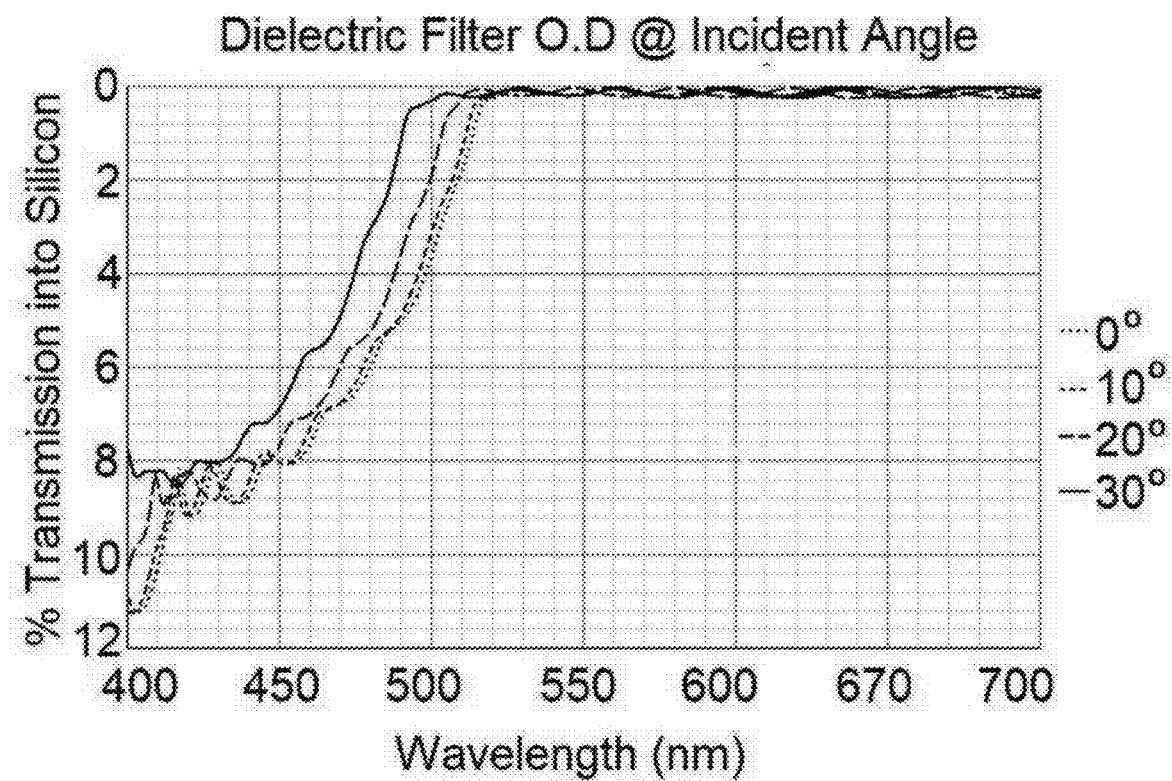
FIG. 17 is a graph illustrating optical characteristics of an interference filter according to one embodiment of the present invention.

FIG. 17 is a graph illustrating optical characteristics of an interference filter according to one embodiment of the present invention.

Referring to FIG. 17, the interference filter is formed by stacking a plurality of transparent layers having different refractive indexes. When incident angle of excitation light is changed, wavelength of light filtered by the interference filter is rapidly changed. For example, when the incident angle is changed from 0 degree to 30 degrees, the cut-off wavelength is decreased by about 50 nm. Generally, since difference of wavelengths between the emission light and the excitation light is only 20 nm to 30 nm, the interference filter cannot be used for the emission filter by the change of the cut-off wavelength of 50 nm.

Figure 18:
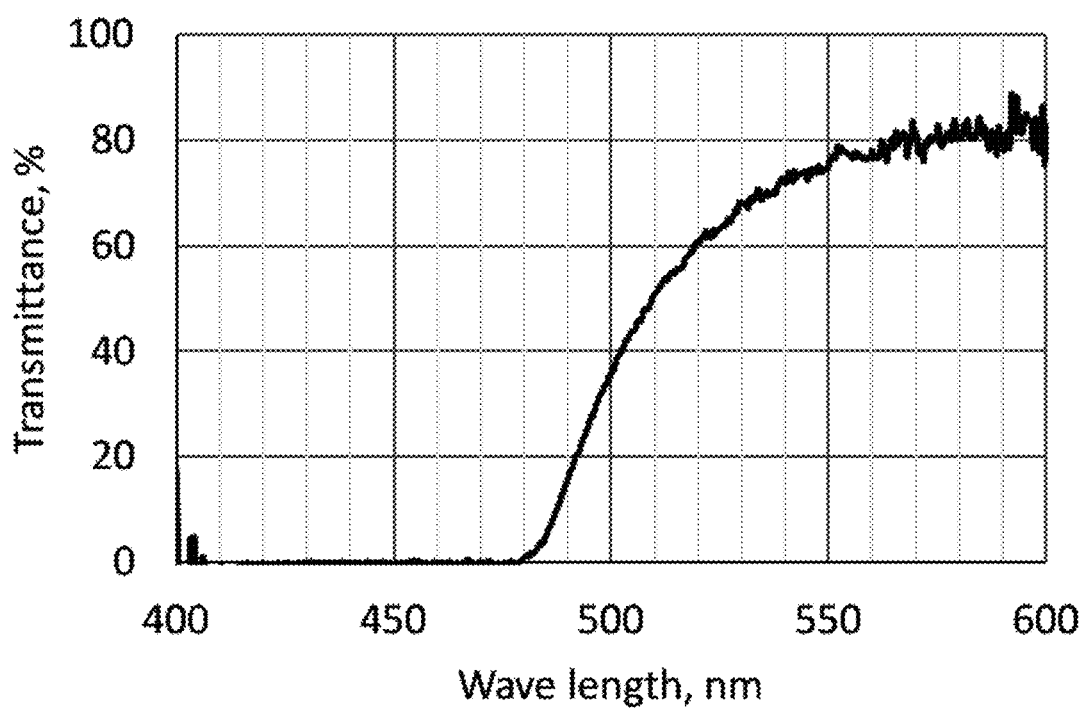
FIG. 18 is a graph illustrating optical characteristics of a wide-angle emission filter according to one embodiment of the present invention.

FIG. 18 is a graph illustrating optical characteristics of a wide-angle emission filter according to one embodiment of the present invention.

Referring to FIG. 18, the wide-angle emission filter of the present invention has the same optical characteristics regardless of incident angles. For example, the wide-angle emission filter has cut-off wavelength of 510 nm. That is, the wide-angle emission filter blocks light having a wavelength smaller than 510 nm and transmits light having a wavelength greater than 510 nm. Referring to Table 1, in a test using fluorescent materials such as FAM, the wide-angle emission filter may be used.

Referring to FIGS. 3 and 18, when excitation light having an intensity of 520 μm was incident into the wide-angle emission filter 100, an intensity of light received into the optical sensor array 210 was 0.001 μm. That is, the wide-angle emission filter 100 had excellent filtering characteristics of 5.72 OD($10^{5.72}$).

Comparative Embodiment 1

Figure 19:
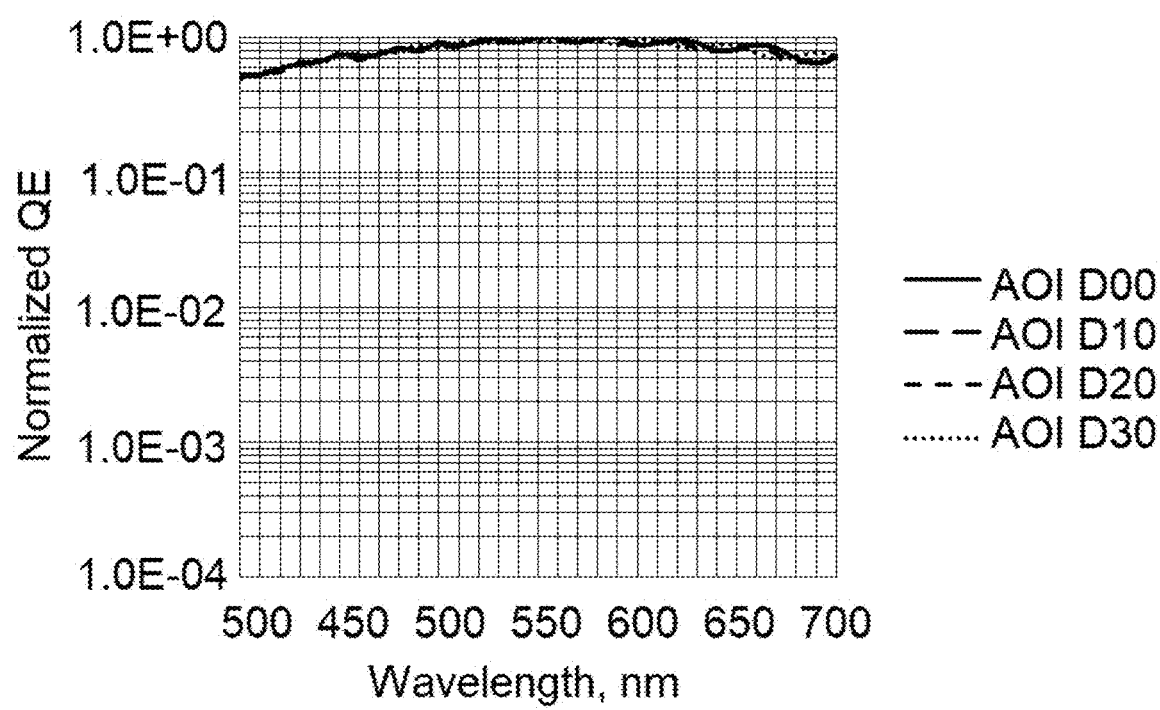
FIG. 19 is a graph illustrating quantum efficiency of optical signal sensed by an optical sensor array based on various incident angles and wavelengths without any emission filter.

FIG. 19 is a graph illustrating quantum efficiency of optical signal sensed by an optical sensor array based on various incident angles and wavelengths without any emission filter.

In particular, the graph illustrates relative quantum efficiency of each wavelength range with respect to quantum efficiency of maximum wavelength range of the optical sensor array.

In FIG. 19, horizontal axis represents wavelength of light sensed by the optical sensor assembly, and vertical axis represents relative quantum efficiency of each wavelength range with respect to quantum efficiency of maximum wavelength range sensed by the optical sensor assembly.

Light is incident into the optical sensor assembly in various incident angles D00, D10, D20, and D30. D00 represents incident angle of 0 degree (vertical direction). D10, D20, and D30 represents incident angles of 10 degrees, 20 degrees, and 30 degrees. In the embodiment of the present invention, the optical sensor assembly of FIG. 1 is substantially the same as shown in FIG. 1 except removing an emission filter.

Referring to FIG. 19, when the wavelength of the sensed light was greater than 630 nm, the quantum efficiency was gradually decreased.

Not intended to limit the scope of the present invention by theory, the reason of the above-phenomenon is that a quantum efficiency of a photodiode is changed by depth of the photodiode in a silicon substrate. Absorption ratio of incident light in the silicon is changed by a wavelength of the incident light. The photodiode of the optical sensor of FIG. 19 was buried in the silicon substrate by a depth of 4 μm. When the wavelength of the incident light was increased, the incident light was not absorbed by the photodiode but transmitted the photodiode.

Comparative Embodiment 2

Figure 20:
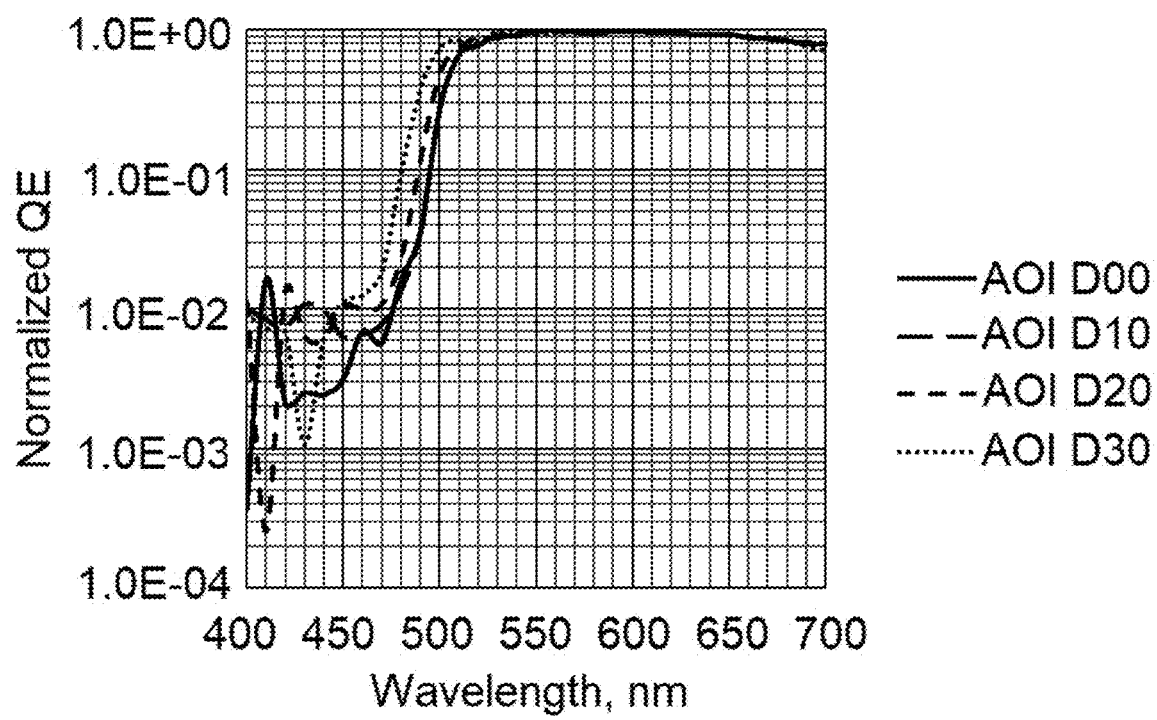
FIG. 20 is a graph illustrating quantum efficiency of optical signal sensed by an optical sensor array based on various incident angles and wavelengths in case of a conventional distributed Bragg reflector (DBF) filter.

FIG. 20 is a graph illustrating quantum efficiency of optical signal sensed by an optical sensor array based on various incident angles and wavelengths in case of a conventional distributed Bragg reflector (DBR) filter.

In FIG. 20, horizontal axis represents wavelength of light sensed by the optical sensor assembly, and vertical axis represents relative quantum efficiency of each wavelength range with respect to quantum efficiency of maximum wavelength range sensed by the optical sensor assembly.

Light is incident into the optical sensor assembly in various incident angles D00, D10, D20, and D30. D00 represents incident angle of 0 degree (vertical direction). D10, D20, and D30 represents incident angles of 10 degrees, 20 degrees, and 30 degrees. The DBR filter was product of Optorontec Inc., Korea. The DBR filter filters light having a wavelength of smaller than 470 nm. In the embodiment of the present invention, the optical sensor assembly of FIG. 1 is substantially the same as shown in FIG. 1 except the DBR filter instead of the emission filter.

Referring to FIG. 20, when the DBR filter was used, quantum efficiency was changed based on incident angles.

When the incident angle was 0 degree (D00), light having a wavelength of less than 470 nm was efficiently blocked. When the incident angle was 10 degrees (D10), light having a wavelength of less than 470 nm was efficiently blocked.

However, when the incident angle is equal to or greater than 20 degrees (D20, D30), the light having the wavelength of 470 nm was not blocked.

Furthermore, even filtered light showed variations in the quantum efficiency with respect to the incident angles. When the quantum efficiency of the filtered light was changed with respect to the incident angle, severe effort may be generated in a precise test such as PCR test, in which small amount of light is sensed.

Embodiment

Figure 21:
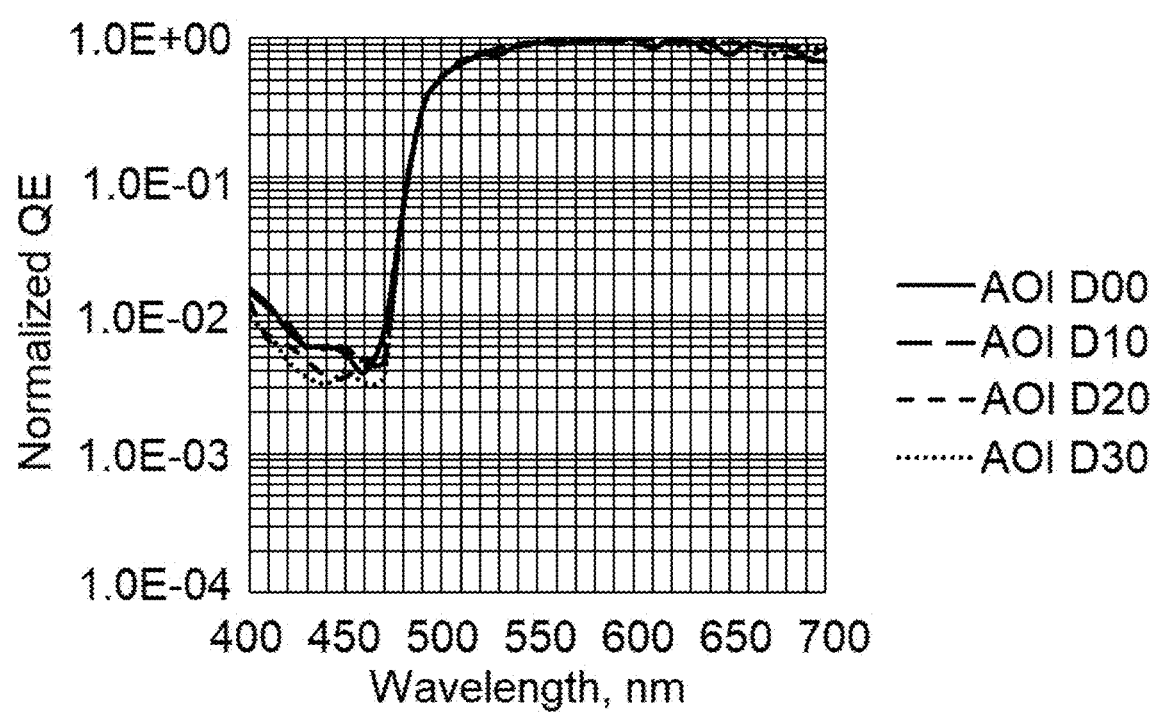
FIG. 21 is a graph illustrating quantum efficiency of optical signal sensed by an optical sensor array based on various incident angles and wavelengths in case of the wide-angle emission filter shown in FIG. 1.

FIG. 21 is a graph illustrating quantum efficiency of optical signal sensed by an optical sensor array based on various incident angles and wavelengths in case of the wide-angle emission filter shown in FIG. 1.

In FIG. 21, horizontal axis represents wavelength of light sensed by the optical sensor assembly, and vertical axis represents relative quantum efficiency of each wavelength range with respect to quantum efficiency of maximum wavelength range sensed by the optical sensor assembly.

Light is incident into the optical sensor assembly in various incident angles D00, D10, D20, and D30. D00 represents incident angle of 0 degree (vertical direction). D10, D20, and D30 represents incident angles of 10 degrees, 20 degrees, and 30 degrees. The wide-angle emission filter filters light having a wavelength of smaller than 470 nm. In the embodiment of the present invention, the optical sensor assembly of FIG. 1 is substantially the same as shown in FIG. 1.

Referring to FIG. 21, when the wide-angle emission filter of FIG. 1 was used, quantum efficiency was not changed regardless of various incident angles.

Although the incident angle was changed from 0 degree to 40 degrees, the light having the wavelength of smaller than 470 nm was efficiently blocked.

Also, the quantum efficiency of the filtered light was not changed regardless of various incident angles. When the quantum efficiency of the filtered light was not changed with respect to the incident angle, error may be decreased in a precise test such as PCR test, in which small amount of light is sensed.

According to the present invention, the semi-solidified photoresist is saturated to be stabilized by the light having the short wavelength such as ultraviolet light, blue light, green light, etc., by absorbing the light having the short wavelength. Thus, the wide-angle emission filter including the semi-solidified photoresist has excellent optical characteristics. That is, in the present invention, the excitation light is firstly blocked by colorant or pigment of the wide-angle emission filter, and is secondly blocked by the semi-solidified photoresist, and thus, the wide-angle emission filter has excellent filtering characteristics in various incident angles. The conventional color filter or the conventional emission filter cannot have the excellent wide-angle filtering characteristics of the present invention.

Also, a complex filter may include the wide-angle emission filter and the interference filter, and thus, an excitation light incident into the interference filter in the vertical direction may be reflected again toward the reaction space. Thus, an amount of the excitation light irradiated into the specimen is increased by twice. Thus, the signal sensed by the optical sensor array is increased by twice, thereby improving sensing accuracy.

Also, when the excitation light is filtered only by an interference filter, an expensive interference filter of OD6 ($10^6$), in which only one millionth of excitation light may pass through the expensive interference filter, is required. However, when the complex filter including the interference filter and the wide-angle emission filter is used, a cheap interference filter of OD2($10^2$) or OD3($10^3$), at which only one hundredth or one thousandth of excitation light may pass through the cheap interference filter, may also be used. The complex filter including the cheap interference filter may have equivalent filtering effect to the expensive interference filter.

Also, the first wide-angle emission filter and the second wide-angle emission filter having different optical characteristics are disposed on the same plane of the optical sensor substrate, and thus, accuracy of the optical sensor array is improved although optical characteristics of the excitation light and the emission light are unknown.

Also, the excitation light is firstly filtered by the semi-solidified photoresist and secondly filtered by the colorant or the pigment, and thus, the wide-angle emission filter has precise cut-off characteristics by the above-mentioned double filtering.

Also, the reaction space, in which the specimen is disposed, is adjacent to the wide-angle emission filter, and thus, quantum efficiency of the optical sensor array is greatly improved.

Also, since the reaction space, in which the specimen is disposed, is adjacent to the wide-angle emission filter, quantum efficiency of the emission light is greatly improved.

Also, the optical part is implanted into the PCR module by the wide-angle emission filter configured to efficiently filter the emission light, and the PCR module is manufactured to be an attachable and detachable module or a disposable module, and thus, a size of the reader system is greatly decreased. Furthermore, the size of the PCR module and the reader system is greatly decreased, and manufacturing cost is decreased.

Also, although the reader system is transported, rearrangement or calibration of relocation of the reader system is unnecessary, and thus, mobility is greatly increased and point-of-care is possible. In particular, detecting systems may be immediately applied to emergency states such as infectious diseases, disaster, identification, etc., thereby minimizing damage.

The present invention has an industrial applicability such a device for inspecting genetic materials, a PCR device, an apparatus for blood test, an apparatus for detecting disease, an apparatus for various researches, an apparatus for preventing disaster, a medical device, an apparatus for livestock, an apparatus for pet, etc.

The foregoing is illustrative of example embodiments and is not to be construed as limiting thereof. Although a few example embodiments have been described, those skilled in the art will readily appreciate that many modifications are possible in the example embodiments without materially departing from the novel teachings and advantages of the present inventive concept. Accordingly, all such modifications are intended to be included within the scope of the present inventive concept as defined in the claims. Therefore, it is to be understood that the foregoing is illustrative of various example embodiments and is not to be construed as limited to the specific example embodiments disclosed, and that modifications to the disclosed example embodiments, as well as other example embodiments, are intended to be included within the scope of the appended claims.

What is claimed is:

1. A wide-angle emission filter comprising:
    a base matrix having a flat shape and including a transparent material, the base matrix not generating fluorescent light or phosphorescent light by an excitation light;
    a photoresist disposed in the base matrix, the photoresist being fixed in a solid state through at least one method selected from the group consisting of thermal hardening, photo hardening, and drying; and
    a colorant disposed in the base matrix and including light having a predetermined wavelength range,
    wherein the wide-angle emission filter filters the excitation light regardless of an incident angle of the excitation light,
    wherein the photoresist comprises a semi-solidified photoresist, which is not completely saturated by light having a short wavelength, and the excitation light is firstly filtered by the colorant, and wherein the semi-solidified photoresist is configured to secondly filter the excitation light to form a secondly filtered semi-solidified photoresist, and
    wherein the photoresist is mixed with the colorant and is disposed in the base matrix, and wherein the photoresist, the colorant, and the base matrix form a same layer.

2. The wide-angle emission filter of claim 1, wherein the wide-angle emission filter is disposable and used for one time test.

3. The wide-angle emission filter of claim 1, wherein the photoresist further comprises a saturated photoresist disposed in the base matrix, which is completely saturated by the excitation light.

4. An optical sensor assembly comprising:
    a wide-angle emission filter configured to filter an excitation light regardless of an incident angle of the excitation light and to transmit emission light having a wavelength greater than the excitation light, the wide-angle emission filter including:
        a base matrix having a flat shape and including a transparent material, the base matrix not generating fluorescent light or phosphorescent light by the excitation light;
        a photoresist disposed in the base matrix, the photoresist being fixed in a solid state through at least one method selected from the group consisting of thermal hardening, photo hardening, and drying; and a colorant disposed in the base matrix and including light having a predetermined wavelength range; and an optical sensor substrate including:
a base substrate having a flat shape and being integrally formed with the wide-angle emission filter; and
an optical sensor array including a plurality of optical sensors buried in an upper portion of the base substrate and arranged in an array shape to sense luminance of the emission light having passed through the wide-angle emission filter, wherein the photoresist comprises a semi-solidified photoresist, which is not completely saturated by light having a short wavelength, and the excitation light is firstly filtered by the colorant, and wherein the semi-solidified photoresist is configured to secondly filter the excitation light to form a secondly filtered semi-solidified photoresist, and wherein the photoresist is mixed with the colorant and is disposed in the base matrix, and wherein the photoresist, the colorant, and the base matrix form a same layer.

5. The optical sensor assembly of claim 4, wherein the optical sensor substrate further comprises:
a temperature sensor disposed adjacent to the wide-angle emission filter to sense temperature; and
a first temperature controlling member disposed under the base substrate to control the temperature.

6. The optical sensor assembly of claim 4, further comprising an interference filter integrally formed on an upper surface of the wide-angle emission filter and being formed by stacking a plurality of refractive layers having different refractive indexes.

7. The optical sensor assembly of claim 6, wherein the interference filter has filtering characteristics of OD3($10^3$), at which one thousandth of incident light pass through the interference filter and remaining of the incident light is blocked by the interference filter, but the optical filter assembly has filtering characteristics of more than or equal to OD5($10^5$), at which one hundred thousandth of incident light pass through the optical filter assembly and remaining of the incident light is blocked by the optical filter assembly.

8. The optical sensor assembly of claim 6, wherein the interference filter comprises a thin film including at least one selected from the group consisting of metal, metal oxide, and nonmetal.

9. The optical sensor assembly of claim 4, further comprising a second wide-angle emission filter formed on the same plane as the wide-angle emission filter and having a second colorant including a material absorbing light having a wavelength different from a wavelength of the colorant.

10. A polymerase chain reaction (PCR) system comprising:
a PCR module including:
a wide-angle emission filter configured to filter an excitation light regardless of an incident angle of the excitation light, the wide-angle emission filter including a photoresist fixed in a solid state through at least one method selected from the group consisting of thermal hardening, photo hardening, and drying; and a colorant including light having a predetermined wavelength range;
an optical sensor substrate including an optical sensor array including a plurality of optical sensors arranged in an array shape to sense luminance of the emission light having passed through the wide-angle emission filter to generate a optical sensing signal;
a reaction space disposed on the wide-angle emission filter to receive a specimen, in which PCR is performed; and
a first temperature controlling part receiving a temperature control signal to control temperature in the reaction space; and
a reader system including:
a central processing unit receiving the optical sensing signal to calculate an amount of gene amplification based on the optical sensing signal to generate the temperature control signal;
a light source generating the excitation light; and
a second temperature controlling part connected to the central processing unit to control temperature of the PCR module, wherein the photoresist comprises a semi-solidified photoresist, which is not completely saturated by light having a short wavelength, and the excitation light is firstly filtered by the colorant, and wherein the semi-solidified photoresist is configured to secondly filter the excitation light to form a secondly filtered semi-solidified photoresist, and wherein the photoresist is mixed with the colorant and is disposed in a base matrix, and wherein the photoresist, the colorant, and the base matrix form a same layer.

11. The PCR system of claim 10, wherein the PCR module is detachably combined with the reader system to be used for only one time test.

* * * * *